United States Patent
Matsumoto et al.

(10) Patent No.: US 7,045,497 B1
(45) Date of Patent: May 16, 2006

(54) USE OF PEPTIDE

(75) Inventors: Hirokazu Matsumoto, Ibaraki (JP); Chieko Kitada, Osaka (JP); Shuji Hinuma, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/868,885

(22) PCT Filed: Dec. 22, 1999

(86) PCT No.: PCT/JP99/07199

§ 371 (c)(1), (2), (4) Date: Jun. 22, 2001

(87) PCT Pub. No.: WO00/38704

PCT Pub. Date: Jul. 6, 2000

(30) Foreign Application Priority Data

Dec. 25, 1998 (JP) .................................. 10-369585

(51) Int. Cl.
*A61K 38/11* (2006.01)
*A61K 38/16* (2006.01)
*C07K 14/00* (2006.01)
*C07H 21/04* (2006.01)

(52) U.S. Cl. .......................... 514/2; 530/350; 530/315; 530/300; 435/7.1; 435/375; 424/198.1; 536/23.51; 536/23.1

(58) Field of Classification Search ................ 530/300, 530/350, 315; 435/7.1, 375; 514/2; 424/198.1; 536/23.51, 23.1
See application file for complete search history.

(56) References Cited

FOREIGN PATENT DOCUMENTS

JP WO 98/58962 6/1998
WO WO 97/24436 * 7/1997

OTHER PUBLICATIONS

Minoru Maruyama, et al., Central Administration of Prolactin-Releasing Peptide Stimulates Oxytocin Release in Rats, *Neuroscience Letters*, 1999, vol. 276, pp193-196.
Minoru Maruyama, et al., Immunocytochemical Localization of Prolactin-Releasing Peptide in the Rat Brain, *Endocrinology*, 1999, vol. 140, pp2326-2333.
Shuji Hinuma, et al., A Prolactin-Releasing Peptide in the Brain, *Nature*, May 21, 1998, vol. 393, pp272-276.
C.J.C. Boersma, et al., Immunocytochemical Localization of Neuropeptide FF (FMRFAmide-Like Peptide) in the Hypothalamo-Neurohypophyseal System of Wistar and Brattleboro Rats by Light and Electron Microscopy, *The Journal of Comparative Neurology*, 1993, vol. 336, pp555-570.

* cited by examiner

*Primary Examiner*—Joseph Murphy
*Assistant Examiner*—Nirmal S. Basi
(74) *Attorney, Agent, or Firm*—David G. Conlin; John B. Alexander; Edwards & Angell, LLP

(57) ABSTRACT

The present invention relates to use of peptide to which G-protein coupled receptor protein recognizes as a ligand. Since the ligand polypeptide of the present invention has a stimulating action on oxytocin secretion, it is useful as a drug for ameliorating, preserving or treating various diseases related to oxytocin secretion such as uterine inertia, atonic hemorrhage, placental expulsion, subinvolution and the like.

2 Claims, 2 Drawing Sheets

Effects of PrRP administration to third venticle of male Wistar rat on oxytocin concentration in blood plasma

USE OF PEPTIDE

TECHNICAL FIELD

The present invention relates to uses of physiologically active peptides. In particular, the present invention relates to oxytocin secretion regulators or the like comprising a ligand polypeptide for a G protein-coupled receptor protein (receptor).

BACKGROUND ART

Many hormones and neurotransmitters regulate biogenic functions through specific receptors present in cell membranes. Most such receptors transmit intracellular signals through the activity of coupled guanine nucleotide-binding proteins (G proteins). These receptors have a common structure with a 7 transmembrane region, and are thus referred to as G protein-coupled receptors or seven transmembrane receptors (7TMR).

Examples of such G protein-coupled receptor proteins include human receptor protein encoded by phGR3 (or GPR10) gene (*Genomics,* 29:335 (1995)) and its corresponding rat receptor protein UHR-1 (*Biochem. Biophy. Res. Commun.*) 209: 606 (1995)).

PrRP (*Nature,* 393:272–276 (1998)) is known as a physiologically active peptide that functions as a ligand for the aforementioned phGR3 and UHR-1.

PrRP has been found to have prolactin-releasing action specific to anterior pituitary hormone in in vitro pituitary cell culture systems (*Nature,* 393:272–276 (1998)), but other types of physiological action, particularly the effects on posterior pituitary hormone, remain unclear. The endogenous regulatory hormone that regulates oxytocin, a posterior pituitary hormone, is currently unknown.

DISCLOSURE OF THE INVENTION

As a result of extensive research to overcome the aforementioned drawbacks, the inventors first prepared two kinds of monoclonal antibodies specific to PrRP with different recognition sites, and prepared a highly sensitive system for assaying PrRP (sandwich-EIA system) (Japanese Patent Application H10-140293, and WO 99/60112). Studies of the tissue distribution of PrRP in rats using this system confirmed the presence of high concentrations of PrRP in the posterior pituitary gland in addition to high concentration distribution in the hypothalmus, etc., as reported in *Nature,* 393:272 (1998). This is assumed to be related to some effect of PrRP on posterior pituitary hormone secretion. The intraventricular administration of PrRP in rats was also found to result in elevated oxytocin concentration in blood, indicating that PrRP has a function in regulating the release of oxytocin.

Specifically, the present invention relates to:

(1) an oxytocin secretion regulator, comprising a ligand peptide, or salt thereof, for a G protein-coupled receptor protein;

(2) an oxytocin secretion regulator according to (1) above, wherein the ligand peptide, or salt thereof, for a G protein-coupled receptor protein is a polypeptide, or an amide or an ester or a salt thereof, containing an amino acid sequence that is the same or substantially the same as the amino acid sequence represented by SEQ ID NO: 44;

(3) an oxytocin secretion regulator according to (2) above, wherein the amino acid sequence represented by SEQ ID NO: 44 is SEQ ID NO: 3, 18, or 32;

(4) an oxytocin secretion regulator according to (1) above, wherein the ligand peptide, or salt thereof, for a G protein-coupled receptor protein is a polypeptide, or an amide or an ester or a salt thereof, containing an amino acid sequence that is the same or substantially the same as the amino acid sequence represented by SEQ ID NO: 45;

(5) an oxytocin secretion regulator according to (4) above, wherein the amino acid sequence represented by SEQ ID NO: 45 is SEQ ID NO: 6, 21, or 35;

(6) an oxytocin secretion regulator according to (1) above, comprising an oxytocin secretion stimulator;

(7) an oxytocin secretion stimulator according to (6) above, comprising a drug for ameliorating, preventing, or treating uterine inertia, atonic hemorrhage, placental expulsion, subinvolution, cesarean section, induced induced abortion, or lacteal retension;

(8) the use of a ligand peptide, or salt thereof, for a G protein-coupled receptor protein in order to regulate oxytocin secretion;

(9) the use of a ligand peptide, or salt thereof, for a G protein-coupled receptor protein in order to manufacture an oxytocin secretion regulator; and

(10) a method for regulating oxytocin secretion, characterized by administering a ligand peptide, or salt thereof, for a G protein-coupled receptor protein to mammals with a disease related to insufficient oxytocin secretion.

BEST MODE FOR CARRYING OUT THE INVENTION

Figure 1:
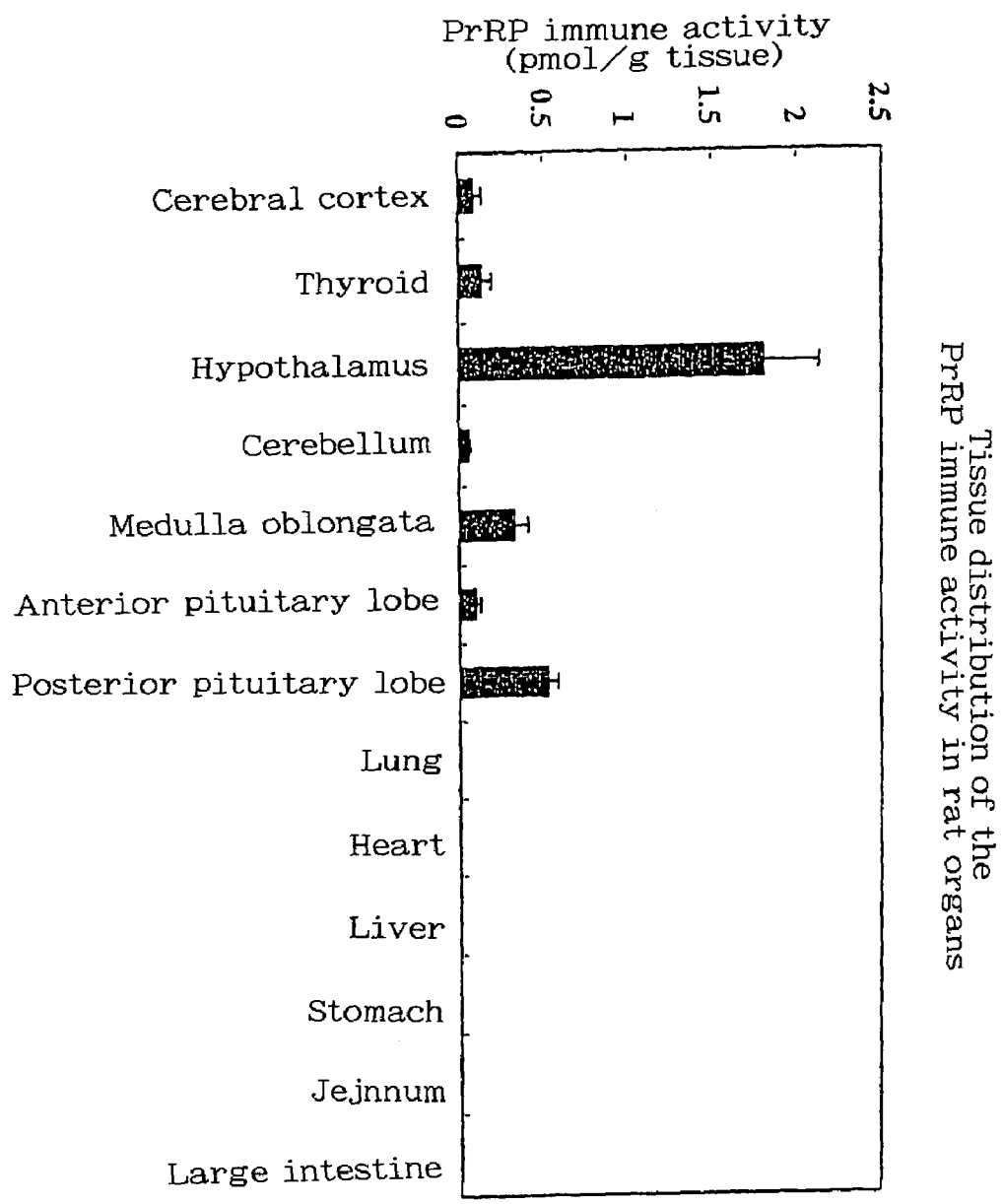
FIG. 1 shows the content of PrRP (19P2-L31) in rat tissue.

Abbreviations for bases, amino acids, and the like in the Specification and figures are based on the IUPAC-IUB Commission on Biochemical Nomenclature and on abbreviations common in the field. Examples are given below. Optical isomers of amino acids are the L form, unless otherwise specified.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
ATP: adenosine triphosphate
EDTA: ethyleendiaminetetraacetic acid
SDS: sodium dodecylsulfate
EIA: enzyme immunoassay
Gly or G: gylcine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid Lys or K: lysine
Arg or R: arginine
His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid
Me: methyl group
Et: ethyl group
Bu: butyl group
Ph: phenyl group Substituents, protective groups, and reagents used in the Specification are represented by the following symbols.
BHA: benzyhydrylamine
pMBHA: p-methylbenzyhydrylamine
Tos: p-toluenesulfonyl
CHO: formyl
HONB: N-hydroxy-5-norbornene-2,3-dicarboxyimide
OcHex: cyclohexyl ester
Bzl: benzyl group
$Cl_2$-Bzl: dichlorobenzyl group
Bom: benzyloxymethyl
Z: benzyloxycarbonyl
Br-Z: 2-bromobenzyloxycarbonyl group
Boc: t-butyloxycarbonyl group
DCM: dichloromethane
HOBt: 1-hydroxybenztriazole
DCC: N,N'-dicyclohexylcarbodiimide
TFA: trifluoroacetic acid
DIEA: diisopropylethylamine
Fmoc: N-9-fluorenylmethoxycarbonyl group
DNP: dinitrophenyl group
Bum: tertiary butoxymethyl group
Trt: trityl group As used herein, "substantially the same" means that activity of the polypeptide (such as the ligand-receptor binding activity), oxytocin secretion-regulating action of the polypeptide (such as action in promoting or inhibiting oxytocin secretion), or the like is essentially the same. Therefore, "substantially the same" amino acid sequence means an amino acid sequence which may be mutated to the extent that activity of the polypeptide (such as the ligand-receptor binding activity), oxytocin secretion-regulating action of the polypeptide (such as action in promoting or inhibiting oxytocin secretion), or the like is essentially the same (the mutation produces no significant changes).

It is generally well known that mutations such as substitutions, deletions, or insertions (additions) of amino acids in a polypeptide sequence often do not bring about (major) significant changes in the physiological or chemical properties of polypeptides. Examples of such substitutions include the substitution of an amino acid with another amino acid having similar properties. It is generally believed that the stronger the similarities between the amino acids that are exchanged, the fewer the differences in properties from the original polypeptide before the substitution as a result of the substitution.

Amino acids may be classified into the following classes, for example, on the basis of similarities in properties: (i) nonpolar (hydrophobic) amino acids such as alanine, leucine, isoleucine, valine, proline, phenylalanine, tryptophan, and methionine; (ii) polar (neutral) amino acids such as glycine, serine, threonine, cysteine, tyrosine, asparagine, and glutamine; (iii) amino acids with a positive charge (basic) such as arginine, lysine, and histidine; and (iv) amino acids with a negative charge (acidic) such as aspartic acid and glutamic acid.

In the present Specification, substituents that are "substantially the same" as the target amino acid in the amino acid sequence are often selected, for example, from other amino acids with similar properties among the same class of amino acids.

In the present invention, polypeptides (mutant polypeptides) obtained as a result of mutation in the amino acid sequence, such as substitutions, deletions, or insertions that bring about (major) significant changes in the physiological or chemical characteristics of the original (unmutated) polypeptide may be regarded as being substantially the same as the original (unmutated) polypeptide which lacks such mutations, and the amino acid sequence of the mutated polypeptide may be regarded as being substantially the same as the amino acid sequence of the original (unmutated) polypeptide.

The constitutive amino acids of the polypeptides in the present invention include both the D and L forms, but the L form is preferred unless otherwise specified.

Polypeptides in the present invention are ligand polypeptides, or their amides or esters or salts, for G protein-coupled receptor proteins, specifically, ligand polypeptides, or their amides or esters or salts, which are capable of binding to G protein-coupled receptor protein. Specific examples include polypeptides or their amides or esters or salts (henceforth sometimes abbreviated as ligand polypeptides or polypeptides) containing an amino acid sequence that is the same as or substantially the same as an amino acid sequence represented by SEQ ID NO: 44 or 45.

As used here, G protein-coupled receptor protein is a receptor protein having a common structure with a 7 cell transmembrane region, which often transmits intracellular signals through the activation of a coupled guanine nucleotide-binding protein.

Preferred examples of the amino acid sequence represented by SEQ ID NO: 44 include amino acid sequences represented by SEQ ID NOs: 3, 18, and 32. The amino acid sequence represented by SEQ ID NO: 32 is particularly preferred.

Preferred examples of the amino acid sequence represented by SEQ ID NO: 45 include amino acid sequences represented by SEQ ID NOs: 6, 21, and 35. The amino acid sequence represented by SEQ ID NO: 35 is particularly preferred.

Examples of the polypeptides in the present invention are those derived from any tissue (e.g., the pituitary, pancreas, brain, kidneys, liver, gonads, thyroid, gall bladder, bone marrow, adrenal gland, skin, muscle, lungs, digestive tract, blood vessels, and heart), cells, and the like from humans and warm-blooded animals (guinea pigs, rats, mice, pigs, goats, cows, monkeys, etc.). Specific examples include those with an amino acid sequence that is the same as or substantially the same as an amino acid sequence represented by SEQ ID NO: 44 or 45, and preferably those with an amino acid sequence the same as or substantially the same as an amino acid sequence represented by SEQ ID NO: 3, 18, or 32, or 6, 21, or 35.

Examples of the ligand polypeptides in the present invention include, in addition to polypeptides with an amino acid sequence represented by SEQ ID NO: 44 or 45, and preferably 3, 18, or 32, or 6, 21, or 35, any polypeptide with an amino acid sequence having about 50 to 99.9% (preferably 70 to 99.9%, even more preferably 80 to 99.9%, and especially 90 to 99.9%) homology with an amino acid sequence represented by SEQ ID NO: 44 or 45, and preferably 3, 18, or 32, or 6, 21, or 35, and more preferably polypeptides having activity substantially the same as that of polypeptides with an amino acid sequence represented by SEQ ID NO: 3, 18, or 32, or 6, 21, or 35. Examples of the activity include the activity of ligand polypeptides, such as receptor-binding activity and signal transduction activity. "Substantially the same" activity means that properties such as receptor-binding activity are the same. The receptor-binding activity may therefore be slightly stronger or weaker. Differences in the molecular weight of the ligand polypeptides are not a problem. Although substantially the same peptides from the same genus of humans or warm-blooded animals may have differences based on amino acid sequences that are not intrinsic to the peptide but are due to differences in a given species (such as individual variation), such peptides with non-intrinsic amino acid sequence-based differences are included in the polypeptides of the present invention.

The manufacturing method and uses of the ligand polypeptides of the present invention are described in further detail below.

Specific examples of the ligand polypeptides in the present invention include polypeptides from rats, cows, humans, or mice, with an amino acid sequence represented by SEQ ID NO: 44 or 45 (in SEQ ID NO: 44, the Xaa at 3 is Thr or Ala, the Xaa at 5 is Arg or Gln, the Xaa at 10 is Ile or Thr, the Xaa at 21 is Thr or Ala, and the Xaa at 22 is Gly or Ser; and in SEQ ID NO: 45, the Xaa at 10 is Thr or Ala, and the Xaa at 11 is Gly or Ser).

The ligand polypeptides of the present invention include polypeptides, or their amides or esters or salts, containing:

(i) amino acid sequences in which 1 to 15, preferably 1 to 10, and even more preferably 1 to 5 amino acids in the amino acid sequence represented by SEQ ID NO: 44 are substituted by other amino acids;

(ii) amino acid sequences in which 1 to 23, preferably 1 to 16, and even more preferably 1 to 11 amino acids in the amino acid sequence represented by SEQ ID NO: 44 are deleted;

(iii) amino acid sequences in which 1 to 15, preferably 1 to 10, and even more preferably 1 to 5 amino acids are added to (inserted into) the amino acid sequence represented by SEQ ID NO: 44; and (iv) amino acid sequences in which constitutive amino acids (particularly the side chains) of polypeptides in (i), (ii), or (iii) have been modified.

The ligand polypeptides of the present invention also include polypeptides, or their amides or esters or salts, containing:

(v) amino acid sequences in which 1 to 10, and preferably 1 to 5 amino acids in the amino acid sequence represented by SEQ ID NO: 45 are substituted by other amino acids;

(vi) amino acid sequences in which 1 to 10, and preferably 1 to 5 amino acids in the amino acid sequence represented by SEQ ID NO: 45 are deleted;

(vii) amino acid sequences in which 1 to 10, and preferably 1 to 5 amino acids are added to (inserted into) the amino acid sequence represented by SEQ ID NO: 45; and (viii) amino acid sequences in which constitutive amino acids (particularly the side chains) of polypeptides in (v), (vi), or (vii) have been modified.

The substitutions, deletions, addition, modifications, and the like to the amino acid sequences as described in (i) through (viii) above can be brought about intentionally or incidentally to allow the ligand polypeptides of the present invention to be mutated (changed) into ligand polypeptides that are stable against heat or protease, or highly active ligand polypeptides in which the inherent physiological activity of ligand polypeptides has been enhanced. The ligand polypeptides or amides or esters thereof, or salts thereof according to the present invention include these mutated ligand polypeptides.

In accordance with the usual procedure for designating peptides, the left terminal in the present Specification is referred to as the N terminal (amino terminal), and the right terminal is referred to as the C terminal (carboxyl terminal).

Examples of modifications to the constitutive amino acids in the polypeptides of the present invention include the conversion of Gln to pyroglutamic acid upon the in vivo cleavage of the N terminal side of Gln.

The α-carboxyl group of C terminal amino acid residues of polypeptides in the present invention, such as polypeptides represented by SEQ ID NO: 44 or 45, is usually a carboxyl group (—COOH) or carboxylate (—COO-), but the carboxyl groups of the C terminal amino acid residues may also be an amide (—CONH$_2$) or ester (—COOR). Examples of R in esters represented by-COOR include $C_{1-6}$ alkyl groups such as methyl, ethyl, n-propyl, isopropyl, or n-butyl, $C_{3-8}$ cycloalkyl groups such as cyclopentyl and cyclohexyl, $C_{6-12}$ aryl groups such as phenyl and α-naphthyl, phenyl-$C_{1-2}$ alkyls such as benzyl and phenethyl, or α-naphthyl-$C_{1-2}$ alkyls such as α-naphthylmethyl and other such $C_{7-14}$ aralkyl groups, as well as pivaloyloxymethyl groups which are commonly used as oral esters.

The polypeptides of the present invention, such as polypeptides represented by SEQ ID NO: 44 or 45, also include polypeptides which have carboxyl group or carboxylate in addition to those in the C terminal, where such groups are amidated or esterified. Examples of esters in such cases are the same as the esters of the aforementioned C terminal amino acid residues.

Particularly desirable ligand polypeptides in the present invention include peptides in which the carboxyl groups of the C terminal amino acid residues are amides. Preferred examples include polypeptides in which the carboxyl groups of the C terminal amino acid residues in polypeptides having an amino acid sequence represented by SEQ ID NO: 3, 6, 18, 21, 32, or 35 are amides.

Although salts with physiologically acceptable bases (such as alkali metals) or acids (organic or inorganic acids) may be used as salts of the polypeptide in the present invention, the physiologically acceptable salts with acids are particularly preferred. Examples of such salts include salts with inorganic acids (e.g., hydrochloric acid, phosphoric acid, hydrobromic acid, and sulfuric acid) or with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The ligand polypeptides of the present invention can be manufactured by (i) techniques for purifying polypeptides from human or warm-blooded animal tissue or cells, or (ii) publicly known synthesis method of polypeptide. They can also be manufactured by (iii) techniques for culturing transformants containing the DNA encoding such polypeptides (to be described later).

(i) When the ligand peptide is manufactured from human or warm-blooded animal tissue or cells, the human or warm-blooded animal tissue or cells should be homogenized and then extracted with acid or the like, and the extract should be purified and isolated in the combination of chromatography such as reverse phase chromatography, ion exchange chromatography, and affinity chromatography.

(ii) The ligand peptide can be manufactured by polypeptide synthesis techniques that are publicly known. Peptides may be synthesized by either solid phase synthesis or liquid phase synthesis, for example. That is, partial peptides or amino acids capable of constructing the ligand polypeptide are condensed with the remainder, and protective groups are eliminated when the product has protective groups, so as to manufacture the target peptide. The following methods in (1) through (5) are publicly known methods for condensation and the removal of protective groups.

(1) M. Bodanszky and M. A. Ondetti, *Peptide Synthesis,* Interscience Publishers, New York (1966)

(2) Schroeder and Luebke, *The Peptide,* Academic Press, new York (1965)

(3) Nobuo Izumiya et al, *Peptide Synthesis Fundamentals and Tests,* Maruzen (1975)

(4) Jimei Yashima and Toshihira Kashiwahara, *Basic Biochemical Tests, Vol.* 1, Protein Chemistry IV, 205 (1977)

(5) *Development of Medical Drugs,* Vol. 14, *Peptide Synthesis,* Hirokawa Shoten, Ed. Jimei Yashima The following is a specific example of the synthesis of the ligand polypeptide in (ii) above.

Commercially available resins for peptide synthesis, which are suitable for amide formation can be used to synthesize amide forms of the ligand peptides. Examples of such resins include chloromethyl resins, hydroxymethyl resins, benzhydrylamine resins, aminomethyl resins, 4-benzyloxybenzyl alcohol resins, 4-methylbenzhydrylamine resins, PAM resins, 4-hydroxymethyl methylphenyl acetamide methyl resins, polyacrylamide resins, 4-(2',4'-dimethoxyphenyl-hydroxymethyl)phenoxy resins, and 4-(2',4'-dimethoxyphenyl-Fmoc aminoethyl)phenoxy resins. Such resins can be used for the condensation of amino acids with suitably protected side chain functional groups and α-amino groups on resin in accordance with various methods of condensation that are publicly known as befits the sequence of the intended peptide. After the reaction, the peptide is excised from the resin, the various protective groups are removed, and the target polypeptide can be obtained. Although various activating reagents that can be used in peptide synthesis may be used for the condensation of such protected amino acids, carbodiimides are particularly preferred. Examples of carbodiimides include DCC, N,N'-diisopropylcarbodiimide, and N-ethyl-N'-(3-dimethylaminopropyl)carbodiimide.

For activation with the above, racemization inhibitors (e.g., HOBt) and protected amino acids can be added directly to the resin, or they can be added in the form of corresponding acid anhydrides or HOBt esters or HOOBt esters to the resin after the activation of the protected amino acids. Solvents which are used for the condensation with resins or the activation of protected amino acids can be suitably selected from solvents which are publicly known to be capable of being used in peptide condensation. Examples of the solvents include acid amides such as N,N-dimethylformamide, N,N-dimethylacetamide, and N-methylpyrrolidone, halogenated hydrocarbons such as methylene chloride and chloroform, alcohol such as trifluoroethanol, sulfoxides such as dimethylsulfoxide, tertiary amines such as pyridine, ethers such as dioxane and tetrahydrofuran, nitriles such as acetonitrile and propionitrile, esters such as methyl acetate and ethyl acetate, and suitable mixtures thereof. The reaction temperature of said reaction can be suitably selected from within the usable range in the publicly known reaction of the formation of peptide bonds, which is usually about −20 to 50° C. The activated amino acid derivatives are usually used in an excess amount of 1.5 to 4 times. The degree to which condensation has been achieved can be determined using a publicly known ninhydrin reaction. When such tests reveal insufficient condensation, the condensation is repeated without removing the protective groups until sufficient condensation has been achieved. When repeated reaction fails to provide sufficient condensation, acetic anhydride or acetyl imidazole may be used for the acetylation of the unreacted amino acids to avoid influencing subsequent reactions.

Examples of protective groups for the amino groups of amino acids as starting material in peptide synthesis include Z, Boc, tert-amyloxycarbonyl, isobornyloxycarbonyl, 4-methoxybenzyloxycarbonyl, Cl-Z, Br-Z, adamantyloxycarbonyl, trifluoroacetyl, phthalyl, formyl, 2-nitrophenylsulfenyl, diphenylphosphinothioyl, and Fmoc. Examples of protective groups for carboxyl groups include the aforementioned $C_{1-6}$ alkyl groups, $C_{3-8}$ cycloalkyl groups, $C_{7-14}$ aralkyl groups, 2-adamantyl, 4-nitrobenzyl, 4-methoxybenzyl, 4-chlorobenzyl, phenacyl groups, and benzyloxycarbonylhydrazide, tert-butoxycarbonylhydrazide, and tritylhydrazide.

The hydroxyl groups of serine and threonine can be protected, for example, by esterification or etherification. Examples of groups that are suitable for esterification include lower ($C_{1-6}$) alkanoyl groups such as acetyl, alloyl groups such as benzoyl, and carbon-derived groups such as benzyloxycarbonyl and ethoxycarbonyl. Examples of groups that are suitable for etherification include benzyl, tetrahydropyranyl, and tert-butyl groups.

Examples of protective groups for phenolic hydroxyl groups of tyrosine include Bzl, $Cl_2$-Bzl, 2-nitrobenzyl, Br-Z, and tert-butyl.

Examples of protective groups for imidazoles of histidine include Tos, 4-methoxy-2,3,6-trimethylbenzenesulfonyl, DNP, benzyloxymethyl, Bum, Boc, Trt, and Fmoc.

Examples of ligand polypeptides in the present invention include any peptides which have a mutated amino acid sequence, provided that the oxytocin-regulating function is the same as that of polypeptides having an amino acid sequence that is the same as or substantially the same as the amino acid sequence represented by SEQ ID NO: 44 or 45. Examples of such peptides include peptides with an amino acid sequence in which 1 to 20 amino acids have been deleted from a peptide having an amino acid sequence represented by SEQ ID NO: 44. Specific examples include (a) a peptide with an amino acid sequence from 2 to 31 of the amino acid sequence represented by SEQ ID NO: 44; (b) a peptide with an amino acid sequence from 3 to 31 of the amino acid sequence represented by SEQ ID NO: 44; (c) a peptide with an amino acid sequence from 4 to 31 of the amino acid sequence represented by SEQ ID NO: 44; (d) a peptide with an amino acid sequence from 5 to 31 of the amino acid sequence represented by SEQ ID NO: 44; (e) a peptide with an amino acid sequence from 6 to 31 of the amino acid sequence represented by SEQ ID NO: 44; (f) a peptide with an amino acid sequence from 7 to 31 of the amino acid sequence represented by SEQ ID NO: 44; (g) a peptide with an amino acid sequence from 8 to 31 of the amino acid sequence represented by SEQ ID NO: 44; (h) a peptide with an amino acid sequence from 9 to 31 of the amino acid sequence represented by SEQ ID NO: 44; (i) a peptide with an amino acid sequence from 10 to 31 of the amino acid sequence represented by SEQ ID NO: 44; (j) a peptide with an amino acid sequence from 11 to 31 of the amino acid sequence represented by SEQ ID NO: 44; (k) a peptide with an amino acid sequence from 12 to 31 of the amino acid sequence represented by SEQ ID NO: 44; (l) a peptide with an amino acid sequence from 13 to 31 of the amino acid sequence represented by SEQ ID NO: 44; (m) a peptide with an amino acid sequence from 14 to 31 of the amino acid sequence represented by SEQ ID NO: 44; (n) a peptide with an amino acid sequence from 15 to 31 of the amino acid sequence represented by SEQ ID NO: 44; (o) a peptide with an amino acid sequence from 16 to 31 of the amino acid sequence represented by SEQ ID NO: 44; (p) a peptide with an amino acid sequence from 17 to 31 of the amino acid sequence represented by SEQ ID NO: 44; (q) a peptide with an amino acid sequence from 18 to 31 of the amino acid sequence represented by SEQ ID NO: 44; (r) a peptide with an amino acid sequence from 19 to 31 of the amino acid sequence represented by SEQ ID NO: 44; (s) a peptide with an amino acid sequence from 20 to 31 of the amino acid sequence represented by SEQ ID NO: 44; and (t) a peptide with an amino acid sequence from 21 to 31 of the amino acid sequence represented by SEQ ID NO: 44.

SEQ ID NOs: 3, 18, and 32, which are preferred examples of the amino acid sequence represented by SEQ ID NO: 44 include the examples given for the amino acid sequence represented by SEQ ID NO: 44.

Examples also include peptides with an amino acid sequence in which 1 to 10 amino acids have been deleted from a peptide having an amino acid sequence represented by SEQ ID NO: 45. Specific examples include (a) a peptide with an amino acid sequence from 2 to 20 of the amino acid sequence represented by SEQ ID NO: 45; (b) a peptide with an amino acid sequence from 3 to 20 of the amino acid sequence represented by SEQ ID NO: 45; (c) a peptide with an amino acid sequence from 4 to 20 of the amino acid sequence represented by SEQ ID NO: 45; (d) a peptide with an amino acid sequence from 5 to 20 of the amino acid sequence represented by SEQ ID NO: 45; (e) a peptide with an amino acid sequence from 6 to 20 of the amino acid sequence represented by SEQ ID NO: 45; (f) a peptide with an amino acid sequence from 7 to 20 of the amino acid sequence represented by SEQ ID NO: 45; (g) a peptide with an amino acid sequence from 8 to 20 of the amino acid sequence represented by SEQ ID NO: 45; (h) a peptide with an amino acid sequence from 9 to 20 of the amino acid sequence represented by SEQ ID NO: 45; (i) a peptide with an amino acid sequence from 10 to 20 of the amino acid sequence represented by SEQ ID NO: 45; and (j) a peptide with an amino acid sequence from 11 to 20 of the amino acid sequence represented by SEQ ID NO: 45.

SEQ ID NOs: 6, 21, and 35 which are preferred examples of the amino acid sequence represented by SEQ ID NO: 45 include the examples given for the amino acid sequence represented by SEQ ID NO: 45.

The ligand polypeptides of the present invention may also be in the form of fused proteins with other proteins (such as publicly known proteins with well known functions or properties).

Examples of DNA encoding the ligand polypeptides in the present invention include any DNA containing a base sequence encoding a polypeptide with an amino acid sequence that is the same as or substantially the same as the amino acid sequence represented by SEQ ID NO: 44 or 45 in the present invention. The DNA can be any of genomic DNA, a genomic DNA library, cDNA derived from tissue or cell, cDNA library derived from tissue or cell, or synthetic DNA. Vectors used for libraries can be any of bacteriophages, plasmids, cosmids, phagimids, or the like. RNA fractions prepared from tissue and cells can be used for direct amplification by RT-PCR (reverse transcription PCR).

Specifically, DNA having a base sequence represented by SEQ ID NO: 2 may be used as the DNA encoding rat whole brain or bovine hypothalamus derived polypeptides having an amino acid sequence represented by SEQ ID NO: 1 or 15.

The R at 129 in SEQ ID NO: 2 is G or A, and the Y at 179 and 240 are C or T. When the Y at 179 is C, the sequence codes for the amino acid sequence represented by SEQ ID NO: 1. When the Y at 179 is T, the sequence codes for the amino acid sequence represented by SEQ ID NO: 15.

DNA having a base sequence represented by SEQ ID NOs: 9, 10, 11, 12, 13, or 14 may be used as the DNA encoding bovine polypeptides with an amino acid sequence represented by SEQ ID NOs: 3, 4, 5, 6, 7, or 8.

The R at 63 in SEQ ID NOs: 9, 10, 11, 12, 13, and 14, and the R at 29 in SEQ ID NOs: 12, 13, 14 are G or A.

DNA having a base sequence represented by SEQ ID NOs: 17, 24, 25, 26, 17, 28, or 29 may be used as the DNA encoding rat polypeptides represented by SEQ ID NOs: 8, 18, 19, 20, 21, 22, or 23.

DNA having a base sequence represented by SEQ ID NOs: 31, 38, 39, 40, 41, 42, or 43 may be used as the DNA encoding human polypeptides represented by SEQ ID NOs: 30, 32, 33, 34, 35, 36, or 37.

As DNA probe, it is preferable to use DNA fragments containing part of the base sequence, such as from 6 to 90 (preferably 6 to 60, more preferably from 9 to 30, and even more preferably from 12 to 30), of the DNA encoding a bovine polypeptide with an amino acid sequence represented by SEQ ID NO: 1 or 15 in the present invention, a rat polypeptide with an amino acid sequence represented by SEQ ID NO: 16, or a human polypeptide with an amino acid sequence represented by SEQ ID NO: 30.

(iii) DNA encoding polypeptides in the present invention can be manufactured by the following genetic engineering techniques.

DNA fully encoding the polypeptides of the present invention should be cloned in the following manner. That is, (1) DNA having a partial base sequence for the polypeptide of interest is synthesized for use as a primer in PCR to amplify DNA fully encoding the polypeptide, or (2) cDNA, genomic DNA, or a DNA library obtained upon the insertion of such DNA fragments into a suitable vector is selected by hybridization with labeled material using synthetic DNA or DNA fragments having part or all of the regions of the ligand polypeptide. The hybridization may be undertaken in accordance with techniques such as that in *Molecular Cloning* ($2^{nd}$ ed. J. Sambrook et al., Cold Spring Harbor Lab. Press (1989)). Commercially available DNA libraries should be used in accordance with the method described in the protocol.

Cloned polypeptide-encoding DNA may be used as such or after digestion with suitable restriction enzymes or after the addition of linker DNA. The DNA may have ATG as the translation start codon on the 5' terminal side, and TAA, TGA, or TAG as the stop codon on the 3' terminal side. The translation start and stop codons can be added using suitable synthetic DNA adapters.

Expression vectors containing DNA with a base sequence encoding such polypeptides can be manufactured by (1) excising target DNA fragments from the DNA containing the DNA encoding a polypeptide of the present invention, and (2) ligating the DNA fragments downstream of a promoter in a suitable expression vector, which is publicly known.

Examples of the vectors include *E. coli* plasmids (such as pBR322, pBR325, pUC12, and pUC13), *Bacillus subtilis* plasmids (such as pUB110, pTP5, and pC194), yeast plasmids (such as pSH19 and pSH15), bacteriophages such as □-phages, and animal viruses such as retroviruses, vaccinia viruses, and baculoviruses. Examples of promoters include any promoters suitably functioning in the host used to express the gene encoding the target polypeptide.

Examples of promoters for when the host is *E. coli* during transformation include the trp promoter, lac promoter, recA promoter, □PL promoter, and lpp promoter. Examples for *Bacillus* hosts include the SPO1 promoter, SPO2 promoter, and penP promoter. Examples for yeast hosts include the PHO5 promoter, PGK promoter, GAP promoter, and ADH promoter. Examples for animal cell preferably include the SV40-derived promoters, retrovirus promoters, metallothionein promoters, heat shock promoters, cytomegalovirus promoters, and SRα promoters. The use of an enhancer is preferred for more efficient expression of the gene encoding the target polypeptide.

A signal sequence suitable for the host may be added as necessary to the N terminal side of the polypeptide or partial peptide. Preferred examples for *E. coli* hosts include alkaline phosphatase signal sequence and OmpA signal sequence. Preferred examples for subtilisin hosts include α-amylase signal sequence and subtilisin signal sequence. Preferred examples for yeast hosts include mating factor α signal sequence and invertase signal sequence. Preferred examples for animal cell hosts include insulin signal sequence, α-interferon signal sequence, and antibody molecule signal sequence. Vectors containing the DNA encoding the polypeptide or partial peptide constructed in this manner are used to manufacture transformants.

Hosts which can be used in transformation include, for example, *E. coli*, *Bacillus*, yeasts, insects, and animal cells.

Examples of *E. coli* include *E. coli* K12-DH1 (*Proc. Natl. Acad. Sci. USA*), 60:160 (1968)), JM103 (*Nucleic Acids Research*, 9:309 (1981)), JA221 (*Journal of Molecular Biology*, 120:517 (1978)), HB101 (*Journal of Molecular Biology*, 41:459 (1969)), and C600 (*Genetics*, 39:440 (1954)).

Specific examples of *Bacillus* include *Bacillus subtilis* MI114 (*Gene*, 24:255 (1983)), and 207-21 (*Journal of Biochemistry*, 95:87 (1984)).

Examples of yeasts include *Saccharomyces cerevisiae* AH22, AH22R⁻, NA87-11A, DKD-5D, and 20B-12.

Examples of insects include silkworm larvae (Maeda et al., *Nature*, 315:592 (1985)).

Examples of animal cells include monkey COS-7 cells, Vero cells, Chinese hamster cells CHO, DHFR gene-deficient Chinese hamster cells CHO (dhfr⁻CHO cells), mouse L cells, mouse myeloma cells, and human FL cells.

*E. coli* can be transformed, for example, by a method such as that in *Proc. Natl. Acad. Sci. USA*, 69:2110 (1972) or *Gene*, 17:107 (1982).

*Bacillus* can be transformed, for example, by a method such as that in *Molecular & General Genetics*, 168:111 (1979).

Yeasts can be transformed, for example, by a method such as that in *Proc. Natl. Acad. Sci. USA*, 75:1929 (1978).

Insect cells can be transformed, for example, by a method such as that in *Bio/Technology*, 6:47 (1988).

Animal cells can be transformed, for example, by a method such as that in *Virology*, 52:456 (1973).

As described above, transformants which have been transformed with expression vectors containing DNA encoding polypeptides can be obtained.

When culturing transformants with *E. coli* or *Bacillus* hosts, liquid media are preferred for the culture, and should be prepared in such a way as to contain carbon sources, nitrogen sources, inorganic material, and other materials necessary for the growth of the transformants. The carbon sources include glucose, dextrins, soluble starches, and sucrose, and the nitrogen sources include inorganic or organic substances such as ammonium salts, nitrates, corn steep liquor, peptone, casein, meat extract, soybean cake, and potato extract. Examples of inorganic materials include calcium chloride, sodium dihydrogen phosphate, and magnesium chloride. Yeast extracts, vitamins, growth stimulating factors, and the like may also be added to the medium as necessary. The medium pH should be a pH at which transformants grow, but the pH should preferably be about 5 to 8.

A preferred media for culturing *E. coli* is M9 medium containing glucose and casamino acid (Miller, *Journal of Experiments in Molecular Genetics*, pp. 431, Cold Spring Harbor Laboratory, New York (1972)). A chemical such as 3β-indoleacrylic acid can be added to enhance the promoter as necessary. In cases where the host is *E. coli*, the culture usually takes about 3 to 24 hours at about 15 to 43° C. The culture can be aerated or stirred as necessary.

In cases where the host is *Bacillus*, the culture usually takes about 6 to 24 hours at about 30 to 40° C. The culture can be aerated or stirred as necessary.

Examples of media for the culture of transformants with yeast hosts include Burkholder minimum medium (K. L. Bostian et al., *Proc. Natl. Acad. Sci. USA*, Vol. 77, p. 4505 (1980), and SD medium containing 0.5% casamino acid (G. A. Bitter et al., *Proc. Natl. Acad. Sci. USA*, Vol. 81, p. 5330 (1984).

The medium pH should be adjusted to about 5 to 8. The culture usually takes about 24 to 72 hours at about 20 to 35° C. The culture can be aerated or stirred as necessary.

Examples of media for the culture of transformants with insect hosts include Grace's Insect Medium (T. C. C. Grace, *Nature*, 195:788 (1962) suitably supplemented with additives such as 10% inactivated bovine serum. The medium pH should be adjusted to about 6.2 to 6.4. The culture usually takes about 3 to 5 days at about 27° C. The culture can be aerated or stirred as necessary.

Examples of media for the culture of transformants with animal cell hosts include MEM medium containing about 5 to 20% fetal calf serum (*Science*, 122:501 (1952), DMEM medium (*Virology*, 8:396 (1959), RPMI 1640 medium (*The Journal of the American Medical Association*, 199:519 (1967), and 199 medium (*Proceedings of the Society for Biological Medicine*, 73:1 (1950). The pH should be about 6 to 8. The culture usually takes about 15 to 60 hours at about 30 to 40° C. The culture can be aerated or stirred as necessary.

Polypeptides can be isolated and purified from the aforementioned cultures (culture broth and cultured bacterial cells or cultured cells) in the following manner, for example.

When polypeptides accumulate in cultured bacterial cells or cultured cells, the bacterial cells or cells are collected by a publicly known method following the culture and are suspended in a suitable buffer, they are disrupted by publicly known ultrasonication, lysozyme treatment and/or by freezing and thawing, etc., and the target polypeptide or partial peptide is then obtained in the form of a crude extract by publicly known methods such as centrifugation, filtration or the like. The buffer may also contain a protein denaturant such as urea or guanidine hydrochloride, or a surfactant such as Triton X-100 (registered trademark (™) by Wako Pure Chemicals).

When the polypeptides are secreted into the culture, the bacterial cells or cells are separated from the supernatant by a publicly known method after the completion of the culture, and the polypeptides can be obtained as the supernatant.

The polypeptides of the present invention contained in the extract or culture supernatant obtained can be purified by a suitable combination of publicly known methods for isolation and purification. Examples of such publicly known methods for isolation and purification include 1) methods featuring the use of the degree of dissolution such as solvent precipitation or salting out, 2) methods primarily making use of differences in molecular weight such as dialysis, ultrafiltration, gel filtration, and SDS-polyacrylamide gel electrophoresis, 3) methods making use of differences in charge such as ion exchange chromatography, 4) methods making use of specific affinity such as affinity chromatography, 5) methods making use of hydrophobic differences such as reverse phase HPLC, and 6) methods making use of differences in isoelectric point, such as isoelectric point electrophoresis and chromatofocusing.

When the polypeptide is obtained in free form, it can be converted to a salt by a publicly known method or a modification thereof. Alternatively, when it is obtained in the form of a salt, it can be converted to free form or another salt by a publicly known method or a modification thereof.

Polypeptides can be modified as desired through the action of suitable protein-modifying enzymes in accordance with a publicly method before or after purification, or the sequence of the polypeptide can be partially removed. Examples of the protein-modifying enzymes include trypsin, chymotrypsin, arginylendopeptidase, protein kinase, and glycosidase. The activity of the resulting mutant polypeptides can be determined by enzyme immunoassay or the like using specific antibodies or receptor-binding tests.

The ligand polypeptides of the present invention have regulating action in oxytocin secretion, that is, action in promoting or inhibiting oxytocin secretion. As will become apparent in the following examples, the ligand polypeptides of the present invention have action in promoting oxytocin secretion, and can thus be used as a prophylactic or remedy for various diseases related to insufficient oxytocin secretion. The ligand polypeptides of the present invention also have strong affinity for receptor proteins, and thus have action in inhibiting oxytocin secretion as a result of desensitization with regard to oxytocin secretion when the dosage is increased. The ligand polypeptides can therefore also be used as prophylactics and remedies for various diseases related to oxytocin oversecretion.

The ligand polypeptides of the present invention can therefore be useful as oxytocin secretion stimulator drugs for ameliorating, preventing, or treating various diseases related to oxytocin secretion, such as uterine inertia, atonic hemorrhage, placental expulsion, subinvolution, cesarean section, induced induced abortion, lacteal retension, induced labor, hypogalactia or hypergalactia or hypergalactia, infertility, dysmenorrhea, miscarriage, and posttraumatic stress syndrome, preferably uterine inertia, atonic hemorrhage, placental expulsion, subinvolution, cesarean section, induced abortion, and lacteal retension, and particularly uterine inertia, atonic hemorrhage, placental expulsion, and subinvolution.

The ligand polypeptides of the present invention are also useful as oxytocin secretion inhibitor drugs for ameliorating, preventing, or treating various diseases related to oxytocin secretion, such as hypertonic labor, hypertonic uterine contractions, fetal distress, uterine rupture, cervical tears, premature birth, Prader-Willi syndrome, and dysmenorrhea, and preferably hypertonic labor, hypertonic uterine contractions, fetal distress, uterine rupture, cervical tears, premature birth, and Prader-Willi syndrome.

The ligand polypeptides of the present invention are also useful as test reagents for studying oxytocin secretion function, and as animal drugs such as lactating stimulators for livestock such as cows, goats, and pigs. Applications may also be anticipated for the production of useful substances that are produced in dairy animals and secreted in their milk.

Ligand polypeptides of the present invention that are used as such pharmaceutical or animal drugs may be employed in the usual manner. For example, they can be orally administered in the form of sugar-coated tablets, capsules, elixirs, microcapsules, and the like, and can be parenterally administered in the form of injections such as sterile solutions with water or other pharmaceutically acceptable liquids, or suspensions. Such preparations can be manufactured, for example, by mixing the polypeptides or their salts in unit dose formulations required for generally recognized preparations, along with physiologically acceptable carriers, flavorings, excipients, vehicles, antiseptics, stabilizers, binders, and the like. The content of the active ingredient in such formulations will give a suitable dose within the indicated range.

Examples of additives miscible with tablets, capsules, and the like include binders such as gelatin, corn starch, tragacanth gum, and gum arabic, excipients such as crystalline cellulose, extenders such as corn starch, gelatin, and alginic acid, lubricants such as magnesium stearate, sweeteners such as sucrose, lactose, and saccharin, and flavors such as peppermint, Akamono oil, or cherry. In the case of unit formulations in the form of capsule preparations, the aforementioned types of material can also include a liquid carrier such as a lipid or an oil. Sterile compositions for injections can be formulated by a common method such as dissolving or suspending a naturally produced vegetable oil or the like such as sesame oil or coconut oil and the active ingredient in a vehicle such as water for injection.

Examples of aqueous solutions for injection include physiological saline, isotonic solutions containing glucose or other adjuvants (such as D-sorbitol, D-mannitol, and sodium chloride). Suitable dissolving aids such as alcohols (such as ethanol), polyalcohols (such as propylene glycol and polyethylene glycol), and nonionic surfactants (such as Polysorbate 80™ and HCO-50) can also be used. Examples of oleaginous solutions include sesame oil and soybean oil. Examples of dissolution aids include benzyl benzoate and benzyl alcohol. Buffers (such as phosphate buffers and sodium acetate buffers), soothing agents (such as benzalkonium and procaine hydrochloride), stabilizers (such as human serum albumin and polyethylene glycol), preservatives (such as benzyl alcohol and phenol), antioxidants, and the like can also be blended. Injections are usually aseptically packaged in suitable ampules.

The resulting preparation is safe and has low toxicity, and can thus be administered, for example, to humans and mammals (such as mice, rats, guinea pigs, rabbits, goats, pigs, cows, cats, dogs, monkeys, sacred baboons, and chimpanzees).

The dosage of the ligand polypeptides in the present invention varies depending on the subjects condition, etc. The orally administered dosage for patients suffering from uterine inertia during labor (per 60 kg body weight) is generally about 0.1 to 100 mg at a time, preferably about 1.0 to 50 mg, and even more preferably about 1.0 to 20 mg. The parenterally administered dosage at a time varies depending on the purpose of administration, the subject's condition, the method of administration, and so forth. Intravenous injections, for example, for patients suffering from uterine inertia (per 60 kg body weight) are generally about 0.01 to 30 mg at a time, preferably about 0.1 to 20 mg, and even more preferably about 0.1 to 10 mg. The dosage for other mammals can also be calculated in terms of 60 kg.

The G protein-coupled receptor proteins (henceforth, sometimes referred to as receptor proteins) or ligand polypeptides used in the present invention can be prepared in accordance with WO 96/05302 or WO 97/24436.

Methods for acquisition and uses of oxytocin secretion regulators comprising compounds or their salts which alter the binding properties between the ligand polypeptides of the present invention for receptor proteins in the present invention and such receptor proteins are described below.

The compounds or their salts which alter the binding properties between the ligand polypeptides for receptor proteins in the present invention and such receptor proteins include compounds and their salts for stimulating the function (such as oxytocin secretion action) of the ligand polypeptides in the present invention, and compounds or their salts for inhibiting the function (such as oxytocin secretion action) of the ligand polypeptides in the present invention.

Since the ligand polypeptides of the present invention have action in regulating oxytocin secretion (such as action in promoting and inhibiting oxytocin secretion), compounds or their salts that promote the oxytocin secretion of the ligand polypeptides in the present invention can be used as oxytocin secretion promoter drugs for ameliorating, preventing, or treating diseases such as uterine inertia, atonic hemorrhage, placental expulsion, subinvolution, cesarean section, induced abortion, lacteal retension, induced labor, hypogalactia or hypergalactia, infertility, dysmenorrhea, miscarriage, and posttraumatic stress syndrome, preferably uterine inertia, atonic hemorrhage, placental expulsion, subinvolution, cesarean section, induced abortion, and lacteal retension, and particularly uterine inertia, atonic hemorrhage, placental expulsion, and subinvolution.

Compounds or their salts that inhibit the oxytocin secretion action of the ligand polypeptides of the present invention are also useful as drugs for ameliorating, preventing, or treating diseases such as hypertonic labor, hypertonic uterine contractions, fetal distress, uterine rupture, cervical tears, premature birth, Prader-Willi syndrome, and dysmenorrhea, and preferably hypertonic labor, hypertonic uterine contractions, fetal distress, uterine rupture, cervical tears, premature birth, and Prader-Willi syndrome.

The ligand polypeptides of the present invention are therefore useful as reagents for screening compounds and their salts which promote or inhibit the function of the ligand polypeptides in the present invention.

Compounds and salts promoting or inhibiting the function of the ligand polypeptides in the present invention can be obtained by screening compounds which modify the bonding properties between G protein-coupled receptor proteins (such as phGR3 and UHR-1 (WO 96/05302 and WO 97/24436)) and the ligand polypeptides of the present invention.

Such screening methods are described below.

A G protein-coupled receptor protein (such as phGR3 and UHR-1 (WO 96/05302 and WO 97/24436)) expression system can be constructed, and a receptor-binding assay system feature the use of the above expression system can be employed for efficient screening of compounds (such as peptides, proteins, nonpeptidic compounds, synthetic compounds, and fermentation products) or their salts which alter the binding properties between the ligand polypeptides of the present invention and G protein-coupled receptor proteins (such as phGR3 and UHR-1 (WO 96/05302 and WO 97/24436)).

Such compounds include: 1) compounds having cell stimulating activity mediated by G protein-coupled receptor proteins (such as activity in promoting or inhibiting the release of arachidonic acid, the release of acetylcholine, the release of intracellular $Ca^{2+}$, the production of intracellular cAMP, the production of intracellular cGMP, the production of inositolphosphoric acid, changes in cell membrane potential, the phosphorylation of intracellular protein, the c-fos activation, and pH reduction); 2) compounds with no such cell-stimulating activity (referred to as receptor protein antagonists); 3) compounds that potentiate the binding strength between the ligand polypeptides of the present invention and G protein-coupled receptor proteins; and 4) compounds that attenuate the binding strength between the ligand polypeptides of the present invention and G protein-coupled receptor proteins.

That is, the present invention provides a method for screening compounds or their salts that alter the binding properties between the ligand polypeptides or their salts in the present invention and receptor proteins or their salts, which is characterized by comparing (i) cases where contact is brought about between receptor proteins or their salts and the ligand polypeptides or their salts in the present invention and (ii) cases where contact is brought about between receptor proteins or their salts and the ligand polypeptides or their salts in the present invention and reagent compounds.

The screening method of the present invention is characterized in that the comparison between cases (i) and (ii) involves assaying the binding of the ligand to the receptor protein, the cell stimulating activity, or the like.

More specifically, the invention provides:

((1)) a method for screening compounds or salts that alter the binding properties between the ligand polypeptides or their salts in the present invention and such receptor proteins or the like, characterized by the assay and comparison of the extent to which labeled ligand polypeptides or salts of the present invention bind to receptor proteins in cases where labeled ligand polypeptides or their salts in the present invention are brought into contact with receptor proteins or the like, and cases where labeled ligand polypeptides or their salts and reagent compounds are brought into contact with the receptor proteins or the like in the present invention;

((2)) a method for screening compounds or salts that alter the binding properties between the ligand polypeptides or their salts of the present invention and such receptor proteins or the like, characterized by the assay and comparison of the extent to which labeled ligand polypeptides or salts of the present invention bind to cells or membrane fractions in cases where labeled ligand polypeptides or their salts of the present invention are brought into contact with cells containing receptor proteins or the like or membrane fractions of such cells, and cases where labeled ligand polypeptides or their salts and reagent compounds are brought into contact with cells containing receptor proteins or the like or membrane fractions of such cells; and ((3)) a method for screening compounds or salts that alter the binding properties between the ligand polypeptides of the present invention and such receptor proteins or the like, by the assay and comparison of the extent to which labeled ligand polypeptides of the present invention bind to receptor proteins in cases where labeled ligand polypeptides of the present invention are brought into contact with receptor proteins or the like expressed on cell membranes as a result of the culture of transformants containing DNA encoding such receptor proteins or the like, and cases where labeled ligand polypeptides of the present invention and reagent compounds are brought into contact with receptor proteins or the like expressed on cell membranes as a result of the culture of transformants containing DNA encoding such receptor proteins or the like.

The aforementioned screening methods are described in further detail below.

Any receptor protein including the above may be used as the receptor protein in the screening methods of the present invention, but cell membrane fractions of mammalian organs containing receptor proteins are preferred. However, because human organs in particular are extremely difficult to obtain, human receptor proteins that are mass produced through expression using recombinants are suitable for use in screening.

Receptor proteins are preferably manufactured by expression of DNA encoding receptors in the mammalian or insect cell. Complementary DNA may be used for DNA fragments encoding the target protein portion, but the options are not necessarily limited to this. For example, gene fragments and synthetic DNA may be used. In order to introduce DNA fragments encoding receptor proteins into host animal cells for efficient expression, the DNA fragment should be inserted downstream of a promoter such as the polyhedrin promoter of a nuclear polyhedrosis virus (NPV) belonging to the baculovirus used with insect hosts, an SV40-derived promoter, a retrovirus promoter, a metallothionein promoter, a human heat shock promoter, a cytomegalovirus promoter, an SRα promoter, or the like. The amount and quality of the expressed receptors can be determined by a publicly known method. This can be done, for example, in accordance with the method in P. Manbi et al., *J. Biol. Chem.*, Vol. 267, pp. 19555–19559 (1992).

Examples of receptor proteins for the aforementioned screening methods include receptor proteins purified by publicly known methods, cells containing such receptor proteins, and membrane fractions of cells containing such receptor proteins.

When cells containing the receptor proteins of the present invention are used in the aforementioned screening methods, the cells may be fixed with glutaraldehyde, formalin, or the like. The cells can be fixed by a publicly known method.

Cells containing receptor proteins refer to host cells expressing the receptor proteins. Preferred examples of host cells include *E. coli, Bacillus subtilis,* yeasts, insect cells, and animal cells.

Cell membrane fractions refer to fractions containing an abundance of cell membranes, obtained by publicly known methods following the disruption of cells. Methods of cell disruption include the method for squeezing cells in a Potter-Elvehjem homogenizer, disruption with a waring blender or Polytron (by Kinematica), disruption by ultrasonication, and the method in which cells are ejected through a narrow nozzle while pressed by a French press. Fractionation by centrifugal force such as centrifugation for fractionation, density gradient centrifugation, and the like is primarily used for fractionation of cell membranes. For example, the disrupted cell suspension is briefly centrifuged (usually about 1 to 10 minutes) at low speed (500 to 3000 rpm), the supernatant is then further centrifuged, usually for 30 minutes to 2 hours at high speed (15,000 to 30,000 rpm), and the resulting precipitate is obtained in the form of membrane fractions. The membrane fractions contain many membrane components such as membrane proteins or cellular phospholipids as well as the expressed receptor proteins.

The amount of receptor protein in the membrane fractions or cells containing receptor proteins is preferably $10^3$ to $10^8$ molecules, and ideally $10^5$ to $10^7$ molecules, per cell. The greater the amount expressed, the higher the ligand binding activity (specific activity) per membrane fraction, the higher the sensitivity of the screening system that can be constructed, and the greater the amount of sample that can be assayed in the same lot.

Suitable receptor protein fractions and labeled ligand polypeptides or their salts of the present invention are needed, for example, in order to screen compounds that alter the binding properties between the ligand polypeptides or their salts of the present invention and receptor proteins.

Preferred examples of receptor protein fractions include natural receptor protein fractions, as well as recombinant receptor protein fractions having the same activity as natural types. As used here, "the same activity" means the same ligand binding activity, signal transducing action, and the like.

Labeled ligands, labeled ligand analog compounds, and the like may be used as the labeled ligands. Examples include ligands labeled with $[^3H]$, $[^{125}I]$, $[^{14}C]$, $[^{35}S]$, and the like.

Specifically, in order to screen for compounds that alter the binding properties between the ligand polypeptides of the present invention and receptor proteins, cell membrane fractions or cells containing the receptor proteins are first suspended in a buffer suitable for screening, so as to prepare a receptor protein preparation. The buffer may be any that does not inhibit binding between the ligand and receptor protein, such as phosphate buffer and Tris-HCl buffer with a pH of between 4 and 10 (and preferably a pH of 6 to 8). A surfactant such as CHAPS, Tween-80™ (Kao-Atlas), digitonin, or deoxycholate can be added to the buffer in order to minimize non-specific binding. A protease inhibitor such as PMSF, leupeptin, E-64 (by Peptide Kenkyusho), or pepstatin can be added to inhibit the degradation of the ligand or receptor by protease. A given amount (5000 cpm to 500,000 cpm) of labeled ligand is added to 0.01 mL to 10 mL of the receptor solution, while $10^{-4}$ M to $10^{-10}$ M test compound is simultaneously coexisted. A reaction tube containing an excess of unlabeled ligand is also prepared to ascertain the extent of non-specific binding (NSB). The reaction is carried out for about 20 minutes to 24 hours, and preferably about 30 minutes to 3 hours, at about 0 to 50° C., and preferably about 4 to 37° C. After the reaction, the solution is filtered with glass fiber filter paper or the like and washed with a suitable amount of the same buffer, and the radioactivity remaining on the glass fiber filter paper is measured with a liquid scintillation counter or γ-counter. Candidates with potential competitive inhibition can be selected, for example, from test compounds with no more than 50% specific binding (B-NSB), where 100% is the count ($B_0$-NSB) obtained by subtracting the non-specific binding (NSB) from the count prevailing in the absence of any competing substance ($B_0$).

Publicly known methods or commercially available assay kits can be used to assay receptor protein-mediated cell-stimulating activity (such as activity in promoting or inhibiting the release of arachidonic acid, the release of acetylcholine, the release of intracellular Ca, the production of intracellular cAMP, the production of intracellular cGMP, the production of inositolphosphoric acid, changes in cell membrane potential, the phosphorylation of intracellular protein, the c-fos activation, and pH reduction) in order to implement the method for screening compounds that alter the binding properties between the ligand polypeptides of the present invention and receptor proteins.

Specifically, cells containing receptor proteins are first cultured in multi-well plates or the like. For screening, the medium or buffer is replaced by fresh medium or a suitable buffer that shows no toxicity to the cells, reagent compounds or the like are added for incubation lasting for a certain period of time, and the cells are then extracted or the supernatant is recovered to quantify the product by a variety of methods. When the production of the substance having the cell-stimulating activity (such as arachidonic acid) is difficult to detect due to degrading enzymes contained in the cells, the assay may be undertaken with the addition of inhibitors for such degrading enzymes. Activity such as the inhibition of cAMP production can be determined in terms of the inhibition of production with regard to cells in which basal production has been increased such as with forskolin.

Cells expressing suitable receptor proteins are necessary for the assay and screening of cell-stimulating activity. Preferred examples of cells expressing receptor proteins include cell lines having natural types of the receptor proteins in the present invention, and cell lines expressing the aforementioned recombinant receptor proteins.

Examples of test compounds include peptides, proteins, non-peptidic compounds, synthetic compounds, fermentation products, cell extracts, vegetable extracts, and animal tissue extracts. Such compounds may be novel compounds or publicly known compounds.

A screening kit for compounds or their salts that alter the binding properties between the ligand polypeptides of the present invention and receptor proteins will include receptor proteins, cells containing receptor proteins, or membrane fractions of cells containing receptor proteins.

Examples of screening kits in the present invention are given below.

1. Screening Reagents ((1)) Assay Buffer and Washing Buffer

Hanks' balanced salt solution (Gibco) supplemented with 0.05% bovine serum albumin (Sigma)

This may be sterilized by filtration with a filter having a pore diameter of 0.45 μm and stored at 4° C., or prepared at the use.

((2)) G Protein-coupled Receptor Preparations

CHO cells expressing receptor proteins are subcultured in a concentration of $5 \times 10^5$ cells/well in 12-well plates, and are cultured for 2 days at 37° C. in 5% CO2 and 95% air.

((3)) Labeled Ligands

Commercially available ligand polypeptides of the present invention labeled with $[^3H]$, $[^{125}I]$, $[^{14}C]$, $[^{35}S]$, or the like Aqueous solution is stored at 4° C. or −20° C., and diluted to 1 μM with assay buffer at use.

((4)) Ligand Reference Solution

The ligands of the present invention are dissolved to a concentration of 1 mM in PBS containing 0.1% bovine serum albumin, and stored at −20° C.

2. Assay Method ((1)) CHO cells expressing receptor proteins cultured in 12-well tissue culturing plates are washed twice with 1 mL of assay buffer, and 490 μL of assay buffer is then added to each well.

((2)) 5 μL of $10^{-3}$ to $10^{-10}$ M reagent compound solution is added, 5 μL of labeled ligand is then added, and a reaction is brought about for 1 hour at room temperature. 5 μL of $10^{-3}$ M ligand is added instead of the test compound in order to ascertain the extent of non-specific binding.

((3)) The reaction solution is removed, and the cells are washed three times with 1 mL of washing buffer. The labeled ligand binding to the cells is dissolved in 0.2 N NaOH-1% SDS and mixed with 4 mL liquid Scintillator A (Wako Pure Chemicals).

((4)) The radioactivity is measured using a liquid scintillation counter (Beckmann), and the percent maximum binding (PMB) is determined using the following equation.

$PMB = [(B-NSB)/(B_0-NSB)] \times 100$

PMB: percent maximum binding
B: value when the sample was added
NSB: non-specific binding
$B_0$: maximum binding Compounds or their salts modifying the binding properties between receptor proteins and the ligand polypeptides of the present invention for receptors in the present invention may be employed in the usual manner as oxytocin secretion regulators. For example, they can be orally administered in the form of sugar-coated tablets, capsules, elixirs, microcapsules, and the like, and can be used in the form of nasal drops or parenterally administered in the form of injections such as sterile solutions with water or other pharmaceutically acceptable liquids, or suspensions. Such preparations can be manufactured, for example, by mixing the compounds or their salts in unit dose formulations required for generally recognized preparations, along with physiologically acceptable carriers, flavorings, excipients, vehicles, antiseptics, stabilizers, binders, and the like. The content of the active ingredient in such formulations will give a suitable dose within the indicated range.

Examples of additives miscible with tablets, capsules, and the like include binders such as gelatin, corn starch, tragacanth gum, and gum arabic, excipients such as crystalline cellulose, extenders such as corn starch, gelatin, and alginic acid, lubricants such as magnesium stearate, sweeteners such as sucrose, lactose, and saccharin, and flavors such as peppermint, Akamono oil, or cherry. In the case of unit formulations in the form of capsule preparations, the aforementioned types of material can also include a liquid carrier such as a lipid or an oil. Sterile compositions for injections can be formulated by a common method such as dissolving or suspending a naturally produced vegetable oil or the like such as sesame oil or coconut oil and the active ingredient in a vehicle such as water for injection.

Examples of aqueous solutions for injection include physiological saline, isotonic solutions containing glucose or other adjuvants (such as D-sorbitol, D-mannitol, and sodium chloride). Suitable dissolving aids such as alcohols (such as ethanol), polyalcohols (such as propylene glycol and polyethylene glycol), and nonionic surfactants (such as Polysorbate 80™ and HCO-50) can also be used. Examples of oleaginous solutions include sesame oil and soybean oil. Examples of dissolution aids include benzyl benzoate and benzyl alcohol. Buffers (such as phosphate buffers and sodium acetate buffers), soothing agents (such as benzalkonium and procaine hydrochloride), stabilizers (such as human serum albumin and polyethylene glycol), preservatives (such as benzyl alcohol and phenol), antioxidants, and the like can also be blended. Injections are usually aseptically packaged in suitable ampules.

The resulting preparation is safe and low toxic, and can thus be administered, for example, to humans and mammals (such as mice, rats, guinea pigs, rabbits, goats, pigs, cows, cats, dogs, monkeys, and chimpanzees).

The dosage of the oxytocin secretion regulators containing the compounds or their salts in the present invention varies depending on the subjects condition, etc. The orally administered dosage for patients suffering from uterine inertia during labor (per 60 kg body weight) is generally about 0.1 to 100 mg at a time, preferably about 1.0 to 50 mg, and even more preferably about 1.0 to 20 mg. The parenterally administered dosage at a time varies depending on the purpose of administration, the subject's condition, the method of administration, and so forth. Intravenous injections, for example, for patients suffering from uterine inertia (per 60 kg body weight) are generally about 0.01 to 30 mg at a time, preferably about 0.1 to 20 mg, and even more preferably about 0.1 to 10 mg. The dosage for other mammals can also be calculated in terms of 60 kg.

The SEQ ID Nos: in the Sequence Listing in the Specification indicate the following sequences.

[SEQ ID NO: 1]
Full length amino acid sequence of bovine hypothalamus derived ligand polypeptide contained in pBOV3.

[SEQ ID NO: 2]
Entire base sequence of the cDNA for bovine hypothalamus derived ligand polypeptide.

[SEQ ID NO: 3]
Amino acid sequence of bovine hypothalamus derived ligand polypeptide, corresponding to the amino acid sequence from 23 to 53 in SEQ ID NO: 1.

[SEQ ID NO: 4]
Amino acid sequence of bovine hypothalamus derived ligand polypeptide, corresponding to the amino acid sequence from 23 to 54 in SEQ ID NO: 1.

[SEQ ID NO: 5]
Amino acid sequence of bovine hypothalamus derived ligand polypeptide, corresponding to the amino acid sequence from 23 to 55 in SEQ ID NO: 1.

[SEQ ID NO: 6]
Amino acid sequence of bovine hypothalamus derived ligand polypeptide, corresponding to the amino acid sequence from 34 to 53 in SEQ ID NO: 1.

[SEQ ID NO: 7]
Amino acid sequence of bovine hypothalamus derived ligand polypeptide, corresponding to the amino acid sequence from 34 to 54 in SEQ ID NO: 1.

[SEQ ID NO: 8]
Amino acid sequence of bovine hypothalamus derived ligand polypeptide, corresponding to the amino acid sequence from 34 to 55 in SEQ ID NO: 1.

[SEQ ID NO: 9]
Base sequence of DNA encoding bovine hypothalamus derived ligand polypeptide (SEQ ID NO: 3)

[SEQ ID NO: 10]
Base sequence of DNA encoding bovine hypothalamus derived ligand polypeptide (SEQ ID NO: 4)

[SEQ ID NO: 11]
Base sequence of DNA encoding bovine hypothalamus derived ligand polypeptide (SEQ ID NO: 5)

[SEQ ID NO: 12]
Base sequence of DNA encoding bovine hypothalamus derived ligand polypeptide (SEQ ID NO: 6)

[SEQ ID NO: 13]
Base sequence of DNA encoding bovine hypothalamus derived ligand polypeptide (SEQ ID NO: 7)

[SEQ ID NO: 14]
Base sequence of DNA encoding bovine hypothalamus derived ligand polypeptide (SEQ ID NO: 8)

[SEQ ID NO: 15]
Full length amino acid sequence of bovine genome derived ligand polypeptide.

[SEQ ID NO: 16]
Full length amino acid sequence of rat ligand polypeptide.

[SEQ ID NO: 17]
Total base sequence of cDNA for rat ligand polypeptide.

[SEQ ID NO: 18]
Amino acid sequence of rat ligand polypeptide, corresponding to the amino acid sequence from 22 to 52 in SEQ ID NO: 16.

[SEQ ID NO: 19]
Amino acid sequence of rat ligand polypeptide, corresponding to the amino acid sequence from 22 to 53 in SEQ ID NO: 16.

[SEQ ID NO: 20]
Amino acid sequence of rat ligand polypeptide, corresponding to the amino acid sequence from 22 to 54 in SEQ ID NO: 16.

[SEQ ID NO: 21]
Amino acid sequence of rat ligand polypeptide, corresponding to the amino acid sequence from 33 to 52 in SEQ ID NO: 16.

[SEQ ID NO: 22]
Amino acid sequence of rat ligand polypeptide, corresponding to the amino acid sequence from 33 to 53 in SEQ ID NO: 16.

[SEQ ID NO: 23]
Amino acid sequence of rat ligand polypeptide, corresponding to the amino acid sequence from 33 to 54 in SEQ ID NO: 16.

[SEQ ID NO: 24]
Base sequence of DNA encoding rat ligand polypeptide (SEQ ID NO: 18)

[SEQ ID NO: 25]
Base sequence of DNA encoding rat ligand polypeptide (SEQ ID NO: 19)

[SEQ ID NO: 26]
Base sequence of DNA encoding rat ligand polypeptide (SEQ ID NO: 20)

[SEQ ID NO: 27]
Base sequence of DNA encoding rat ligand polypeptide (SEQ ID NO: 21)

[SEQ ID NO: 28]
Base sequence of DNA encoding rat ligand polypeptide (SEQ ID NO: 22)

[SEQ ID NO: 29]
Base sequence of DNA encoding rat ligand polypeptide (SEQ ID NO: 23)

[SEQ ID NO: 30]
Full length amino acid sequence of human ligand polypeptide.

[SEQ ID NO: 31]

Total base sequence of cDNA for human ligand polypeptide.

[SEQ ID NO: 32]

Amino acid sequence of human ligand polypeptide, corresponding to the amino acid sequence from 23 to 53 in SEQ ID NO: 30.

[SEQ ID NO: 33]

Amino acid sequence of human ligand polypeptide, corresponding to the amino acid sequence from 23 to 54 in SEQ ID NO: 30.

[SEQ ID NO: 34]

Amino acid sequence of human ligand polypeptide, corresponding to the amino acid sequence from 23 to 55 in SEQ ID NO: 30.

[SEQ ID NO: 35]

Amino acid sequence of human ligand polypeptide, corresponding to the amino acid sequence from 34 to 53 in SEQ ID NO: 30.

[SEQ ID NO: 36]

Amino acid sequence of human ligand polypeptide, corresponding to the amino acid sequence from 34 to 54 in SEQ ID NO: 30.

[SEQ ID NO: 37]

Amino acid sequence of human ligand polypeptide, corresponding to the amino acid sequence from 34 to 55 in SEQ ID NO: 30.

[SEQ ID NO: 38]

Base sequence of DNA encoding human ligand polypeptide (SEQ ID NO: 32).

[SEQ ID NO: 39]

Base sequence of DNA encoding human ligand polypeptide (SEQ ID NO: 33).

[SEQ ID NO: 40]

Base sequence of DNA encoding human ligand polypeptide (SEQ ID NO: 34).

[SEQ ID NO: 41]

Base sequence of DNA encoding human ligand polypeptide (SEQ ID NO: 35).

[SEQ ID NO: 42]

Base sequence of DNA encoding human ligand polypeptide (SEQ ID NO: 36).

[SEQ ID NO: 43]

Base sequence of DNA encoding human ligand polypeptide (SEQ ID NO: 37).

[SEQ ID NO: 44]

Amino acid sequence of ligand polypeptide in present invention, wherein the Xaa at 10 is Ala or Thr, the Xaa at 11 is Gly or Ser, and the Xaa at 21 is H, Gly, or GlyArg.

[SEQ ID NO: 45]

Amino acid sequence of ligand polypeptide in present invention, wherein the Xaa at 10 is Thr or Ala, and the Xaa at 11 is Gly or Ser.

Examples and reference examples are given below to illustrate the present invention in further detail, but the scope of the present invention is not limited by these examples.

EXAMPLE 1

Determination of the Distribution of PrRP (19P2-L31) in Rat Organs

Male Wistar rats were decapitated, the pancreas organs were delivered to weigh the tissue, and the organs were immediately frozen using liquid nitrogen. PrRP (19P2-L31) was extracted from the organs by adding 10-fold distilled water to each of the organs, which were heat treated for 10 minutes in boiling water to inactivate the protease and then cooled in ice. Glacial acetic acid (final concentration of 1 N), pepstatin (final concentration of 1 μg/mL), and phosphoramidone (final concentration of 100 μg/mL) were added, and then the mixture was homogenized for 1 minute in a Polytron homogenizer (Kinematica), and then centrifuged for 30 minutes at 17,000×g. The resulting organ extract was concentrated with a 265 mg of Sep-Pak Plus C18 cartridge (Waters), and PrRP (19P2-L31) described in Nature, Vol. 393, pp. 272–276 (1998) and WO 97/24436 was quantified using the previously reported sandwich EIA system (Japanese Patent Application H10-140293 and WO 99/60112). 4 mL of 86% ethanol containing 4% acetic acid, 4 mL of methanol, 4 mL of distilled water, and 4 mL of 4% acetic acid were poured, in that sequence, to the activated Sep-Pak Plus C18 cartridge, to which the extract was added, and the cartridge was then washed with 10 mL of distilled water and then eluted with 4 mL of 86% ethanol containing 4% acetic acid and 4 mL of methanol to concentrate the extract in a nitrogen stream at 37° C. The concentrated fractions were reconstructed in 0.25 mL of buffer C (0.02 M phosphate buffer (pH 7) containing 10% Bloc Ace, 0.2% BSA, 0.4 M NaCl, and 0.05% CHAPS (3-[(3-cholamidopropyl)dimethylammonio]propanesulfonic acid)) and quantified by sandwich EIA. The results are shown in FIG. 1. PrRP (19P2-L31) immune activity of 0.53±0.06 pmol/g tissue (mean±SEM, n=5) was detected in rat posterior pituitary gland.

EXAMPLE 2

Effect of Third Intraventricular Administration of PrRP (19P2-L31) on Amount of Oxytocin Secreted in Plasma Mature male Wistar rats (weighing 350 to 380 g at the time of surgery) were anesthetized by intraperitoneal administration of 50 mg/kg pentobarbital, and were fixed in a rat brain stereotactic instrument. The brace bar was lowered 3.3 mm from the intra-oral line. The cranial bone was exposed, and a dental drill was used to perforate the bone in order to implant a guide cannula AG-12 (inside diameter 0.4 mm, outside diameter 0.5 mm, Eicom) into the third ventricle. Anchor screws were embedded in four locations around the cannula. The stainless steel guide cannula AG-12 was inserted to a position at the top of the third ventricle. Position coordinates were AP: +7.1 mm, L: 0.0 mm, and H: +2.0 mm, in accordance with the atlas of Paxinos and Watson (1986). The guide cannula was secured to the cranial bone using instant adhesive, dental cement, and the anchor screws. A stainless steel dummy cannula AD-12 (outside diameter 0.35 mm, Eicom) was inserted into the guide cannula and secured with a cap nut (Eicom). Following surgery, the rats were bred in individual cages.

Animal were given about 1 week to recover after implantation of the guide cannulas, and blood was drawn as the animals were allowed to move freely. Rats which had undergone the aforementioned surgery were anesthetized by intraperitoneal administration of 50 mg/kg pentobarbital. The animals were positioned on their backs on necropsy pads, and the jugular vein on the left side was exposed. Polyethylene tubes SP 35 (inside diameter 0.5 mm, outside diameter 0.9 mm, Natsume Seisakusho) were cut to a length of about 30 cm, were filled with physiological saline containing 200 units/mL heparin, and were inserted about 4.5 cm into the jugular veins and secured. The other end of the tubes were passed under the dorsal skin and exposed from the cervical region (dorsal side).

Figure 2:
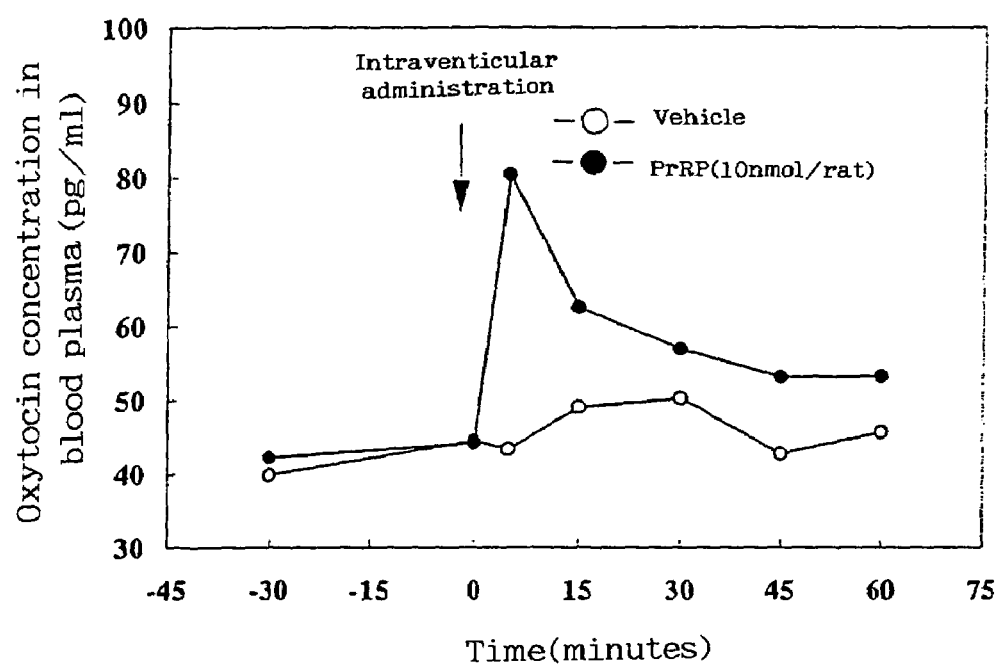
FIG. 2 shows the changes in the oxytocin concentration in blood during the intraventricular administration of 10 nmol PrRP (19P2-L31) to rats.

One night after surgery, 400 µL of blood was drawn using a 1 mL tuberculin syringe and 25 gauge needle (both by Terumo) 30 minutes before administration of PrRP (19P2-L31). 20 µL of physiological saline containing 200 units/mL heparin was introduced into the syringe to prevent blood coagulation. The cap nut and dummy cannula attached to the cranial bone of the rats were removed, and in their place a stainless steel microinjection cannula (inside diameter 0.17 mm, outside diameter 0.35 mm, Eicom) connected to a Teflon tube (50 cm long, inside diameter 0.1 mm, outside diameter 0.35 mm, Eicom) was inserted. The length of the microinjection cannula was adjusted so that the tip was exposed 1 mm from the guide cannula. One end of the Teflon tube was connected to a microsyringe pump, and either phosphate-buffered physiological saline containing 0.5% BSA in which PrRP (19P2-L31) had been dissolved or phosphate-buffered physiological saline containing 0.5% bovine serum albumin (BSA) was injected at a rate of 5 µL/min into the third ventricle. 15 minutes after the injection, the microinjection cannula was removed, and the dummy cannula was again secured with the cap nut. 400 µL samples of blood were drawn from the jugular vein immediately before and 5, 15, 30, 45, and 60 minutes after the intraventricular administration. The drawn blood was centrifuged (5,000 rpm, 10 min) using a high speed cooled microcentrifuge (MR-150, Tomy Seiko), and the supernatant (plasma) was recovered. The oxytocin in the plasma was assayed by radioimmunoassay (Peninsula). As shown in FIG. 2, the oxytocin concentration in blood was about 2 times higher than the control group 5 minutes after the administration of 10 nmol PrRP (19P2-L31) to the third ventricle.

PREPARATION EXAMPLE 1

50 mg of the compound obtained in Example 2 was dissolved in 50 mL of Japan Pharmacopoeia distilled water, and Japan Pharmacopoeia distilled water was added to bring the total to 100 mL. The solution was aseptically filtered, and 1 mL portions of the solution were then used to fill injection vials under aseptic conditions, lyophilized, and sealed.

PREPARATION EXAMPLE 2

100 mg of the compound obtained in Example 2 was dissolved in 50 mL of Japan Pharmacopoeia distilled water, and Japan Pharmacopoeia distilled water was added to bring the total to 100 mL. The solution was aseptically filtered, and 1 mL portions of the solution were then used to fill injection vials under aseptic conditions, lyophilized, and sealed.

INDUSTRIAL APPLICABILITY

The ligand polypeptides of the present invention have action in regulating oxytocin secretion (action in promoting and inhibiting oxytocin secretion). That is, the ligand polypeptides in the present invention have action in promoting oxytocin secretion, and thus can be used as prophylactics and remedies for various diseases related to insufficient oxytocin secretion. The ligand polypeptides in the present invention also have strong affinity for receptor proteins, and thus have action in inhibiting oxytocin secretion as a result of desensitization with regard to oxytocin secretion when the dosage is increased. The ligand polypeptides can therefore also be used as prophylactics and remedies for various diseases related to oxytocin oversecretion.

Therefore, the ligand polypeptides of the present invention can be useful as oxytocin secretion stimulating drugs for ameliorating, preventing, or treating various diseases related to oxytocin secretion, such as uterine inertia, atonic hemorrhage, placental expulsion, subinvolution, cesarean section, induced abortion, lacteal retension, induced labor, hypogalactia or hypergalactia, infertility, dysmenorrhea, miscarriage, and posttraumatic stress syndrome, preferably uterine inertia, atonic hemorrhage, placental expulsion, subinvolution, cesarean section, induced abortion, and lacteal retension, and particularly uterine inertia, atonic hemorrhage, placental expulsion, and subinvolution.

The ligand polypeptides of the present invention are also useful as oxytocin secretion depressor, and drugs for ameliorating, preventing, or treating various diseases related to oxytocin secretion, such as hyperdynamia uteri, hypertonic uterine contractions, fetal distress, uterine rupture, cervical tears, premature birth, Prader-Willi syndrome, and dysmenorrhea, and preferably hyperdynamia uteri, hypertonic uterine contractions, fetal distress, uterine rupture, cervical tears, premature birth, and Prader-Willi syndrome.

The ligand polypeptides of the present invention are also useful as test reagents for studying oxytocin secretion function, and as animal drugs such as lactating stimulators for livestock such as cows, goats, and pigs. Applications may also be anticipated for the production of useful substances that are produced in dairy animals and secreted in their milk.

What is claimed is:

1. A method of regulating oxytocin secretion comprising administering to a patient in need of oxytocin secretion regulation, an effective amount of an isolated and purified oxytocin secretion regulator, comprising a ligand peptide, or salt thereof, for a G protein-coupled receptor protein, phGR3, wherein the ligand peptide, or salt thereof, for a G protein-coupled receptor protein is a polypeptide, or an amide or an ester or a salt thereof, comprising an amino acid sequence that has the amino acid sequence represented by SEQ ID NO: 44, wherein the oxytocin secretion regulator is an oxytocin secretion promoter.

2. The method of claim 1, wherein the amino acid sequence represented by SEQ ID NO: 44 is selected from the group consisting of SEQ ID NO: 3, 18, and 32.

* * * * *

SEQUENCE LISTING

<160> NUMBER OF SEQ ID NOS: 45

<210> SEQ ID NO 1
<211> LENGTH: 98
<212> TYPE: PRT
<213> ORGANISM: Bovine

<400> SEQUENCE: 1

Met Lys Ala Val Gly Ala Trp Leu Leu Cys Leu Leu Leu Gly Leu

-continued

```
                1               5                  10                 15
Ala Leu Gln Gly Ala Ala Ser Arg Ala His Gln His Ser Met Glu Ile
                    20                  25                  30

Arg Thr Pro Asp Ile Asn Pro Ala Trp Tyr Ala Gly Arg Gly Ile Arg
                35                  40                  45

Pro Val Gly Arg Phe Gly Arg Arg Ala Ala Pro Gly Asp Gly Pro
     50                  55                  60

Arg Pro Gly Pro Arg Val Pro Ala Cys Phe Arg Leu Glu Gly
 65                  70                  75                  80

Ala Glu Pro Ser Arg Ala Leu Pro Gly Arg Leu Thr Ala Gln Leu Val
                    85                  90                  95

Gln Glu

<210> SEQ ID NO 2
<211> LENGTH: 294
<212> TYPE: DNA
<213> ORGANISM: Bovine

<400> SEQUENCE: 2
atgaaggcgg tgggggcctg gctcctctgc ctgctgctgc tgggcctggc cctgcagggg      60
gctgccagca gagcccacca gcactccatg gagatccgca ccccgacat caaccctgcc     120 tggtacgcrg ccgtgggat ccggcccgtg ggccgcttcg ccggcgaag agctgcccyg      180 ggggacggac ccaggcctgg ccccggcgt gtgccggcct gcttccgcct ggaaggcggy    240
gctgagccct cccgagccct cccggggcgg ctgacggccc agctggtcca ggaa         294

<210> SEQ ID NO 3
<211> LENGTH: 31
<212> TYPE: PRT
<213> ORGANISM: Bovine

<400> SEQUENCE: 3

Ser Arg Ala His Gln His Ser Met Glu Ile Arg Thr Pro Asp Ile Asn
 1               5                  10                  15

Pro Ala Trp Tyr Ala Gly Arg Gly Ile Arg Pro Val Gly Arg Phe
                20                  25                  30

<210> SEQ ID NO 4
<211> LENGTH: 32
<212> TYPE: PRT
<213> ORGANISM: Bovine

<400> SEQUENCE: 4

Ser Arg Ala His Gln His Ser Met Glu Ile Arg Thr Pro Asp Ile Asn
 1               5                  10                  15

Pro Ala Trp Tyr Ala Gly Arg Gly Ile Arg Pro Val Gly Arg Phe Gly
                20                  25                  30

<210> SEQ ID NO 5
<211> LENGTH: 33
<212> TYPE: PRT
<213> ORGANISM: Bovine

<400> SEQUENCE: 5

Ser Arg Ala His Gln His Ser Met Glu Ile Arg Thr Pro Asp Ile Asn
 1               5                  10                  15

Pro Ala Trp Tyr Ala Gly Arg Gly Ile Arg Pro Val Gly Arg Phe Gly
                20                  25                  30
```

Arg
33

<210> SEQ ID NO 6
<211> LENGTH: 20
<212> TYPE: PRT
<213> ORGANISM: Bovine

<400> SEQUENCE: 6

Thr Pro Asp Ile Asn Pro Ala Trp Tyr Ala Gly Arg Gly Ile Arg Pro
1               5                   10                  15

Val Gly Arg Phe
            20

<210> SEQ ID NO 7
<211> LENGTH: 21
<212> TYPE: PRT
<213> ORGANISM: Bovine

<400> SEQUENCE: 7

Thr Pro Asp Ile Asn Pro Ala Trp Tyr Ala Gly Arg Gly Ile Arg Pro
1               5                   10                  15

Val Gly Arg Phe Gly
            20

<210> SEQ ID NO 8
<211> LENGTH: 22
<212> TYPE: PRT
<213> ORGANISM: Bovine

<400> SEQUENCE: 8

Thr Pro Asp Ile Asn Pro Ala Trp Tyr Ala Gly Arg Gly Ile Arg Pro
1               5                   10                  15

Val Gly Arg Phe Gly Arg
            20

<210> SEQ ID NO 9
<211> LENGTH: 93
<212> TYPE: DNA
<213> ORGANISM: Bovine

<400> SEQUENCE: 9
agcagagccc accagcactc catggagatc cgcaccccg acatcaaccc tgcctggtac      60
gcrggccgtg ggatccggcc cgtgggccgc ttc                                  93

<210> SEQ ID NO 10
<211> LENGTH: 96
<212> TYPE: DNA
<213> ORGANISM: Bovine

<400> SEQUENCE: 10
agcagagccc accagcactc catggagatc cgcaccccg acatcaaccc tgcctggtac      60
gcrggccgtg ggatccggcc cgtgggccgc ttcggc                               96

<210> SEQ ID NO 11
<211> LENGTH: 99
<212> TYPE: DNA
<213> ORGANISM: Bovine

<400> SEQUENCE: 11
agcagagccc accagcactc catggagatc cgcaccccg acatcaaccc tgcctggtac      60

```
gcrggccgtg ggatccggcc cgtgggccgc ttcggccgg                               99
```

<210> SEQ ID NO 12
<211> LENGTH: 60
<212> TYPE: DNA
<213> ORGANISM: Bovine

<400> SEQUENCE: 12

```
accccccgaca tcaaccctgc ctggtacgcr ggccgtggga tccggcccgt gggccgcttc      60
```

<210> SEQ ID NO 13
<211> LENGTH: 63
<212> TYPE: DNA
<213> ORGANISM: Bovine

<400> SEQUENCE: 13

```
accccccgaca tcaaccctgc ctggtacgcr ggccgtggga tccggcccgt gggccgcttc      60
ggc                                                                    63
```

<210> SEQ ID NO 14
<211> LENGTH: 66
<212> TYPE: DNA
<213> ORGANISM: Bovine

<400> SEQUENCE: 14

```
accccccgaca tcaaccctgc ctggtacgcr ggccgtggga tccggcccgt gggccgcttc      60
ggccgg                                                                 66
```

<210> SEQ ID NO 15
<211> LENGTH: 98
<212> TYPE: PRT
<213> ORGANISM: Bovine

<400> SEQUENCE: 15

```
Met Lys Ala Val Gly Ala Trp Leu Leu Cys Leu Leu Leu Gly Leu
 1               5                  10                  15

Ala Leu Gln Gly Ala Ala Ser Arg Ala His Gln His Ser Met Glu Ile
                20                  25                  30

Arg Thr Pro Asp Ile Asn Pro Ala Trp Tyr Ala Gly Arg Gly Ile Arg
         35                  40                  45

Pro Val Gly Arg Phe Gly Arg Arg Ala Ala Leu Gly Asp Gly Pro
     50                  55                  60

Arg Pro Gly Pro Arg Arg Val Pro Ala Cys Phe Arg Leu Glu Gly Gly
 65                  70                  75                  80

Ala Glu Pro Ser Arg Ala Leu Pro Gly Arg Leu Thr Ala Gln Leu Val
                85                  90                  95

Gln Glu
```

<210> SEQ ID NO 16
<211> LENGTH: 83
<212> TYPE: PRT
<213> ORGANISM: Rat

<400> SEQUENCE: 16

```
Met Ala Leu Lys Thr Trp Leu Leu Cys Leu Leu Leu Ser Leu Val
 1               5                  10                  15

Leu Pro Gly Ala Ser Ser Arg Ala His Gln His Ser Met Glu Thr Arg
                20                  25                  30

Thr Pro Asp Ile Asn Pro Ala Trp Tyr Thr Gly Arg Gly Ile Arg Pro
```

35                  40                  45
Val Gly Arg Phe Gly Arg Arg Ala Thr Pro Arg Asp Val Thr Gly
        50                  55                  60

Leu Gly Gln Leu Ser Cys Leu Pro Leu Asp Gly Arg Thr Lys Phe Ser
65                  70                  75                  80

Gln Arg Gly

<210> SEQ ID NO 17
<211> LENGTH: 249
<212> TYPE: DNA
<213> ORGANISM: Rat

<400> SEQUENCE: 17
atggccctga agacgtggct tctgtgcttg ctgctgctaa gcttggtcct cccagggggct      60 tccagccgag cccaccagca ctccatggag acaagaaccc ctgatatcaa tcctgcctgg     120
tacacgggcc gcgggatcag gcctgtgggc cgcttcggca ggagaagggc aaccccgagg     180
gatgtcactg gacttggcca actcagctgc ctcccactgg atggacgcac caagttctct     240
cagcgtgga                                                              249

<210> SEQ ID NO 18
<211> LENGTH: 31
<212> TYPE: PRT
<213> ORGANISM: Rat

<400> SEQUENCE: 18

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 19
<211> LENGTH: 32
<212> TYPE: PRT
<213> ORGANISM: Rat

<400> SEQUENCE: 19

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe Gly
            20                  25                  30

<210> SEQ ID NO 20
<211> LENGTH: 33
<212> TYPE: PRT
<213> ORGANISM: Rat

<400> SEQUENCE: 20

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe Gly
            20                  25                  30

Arg

<210> SEQ ID NO 21
<211> LENGTH: 20
<212> TYPE: PRT
<213> ORGANISM: Rat

<400> SEQUENCE: 21

```
Thr Pro Asp Ile Asn Pro Ala Trp Tyr Thr Gly Arg Gly Ile Arg Pro
 1               5                  10                  15

Val Gly Arg Phe
            20

<210> SEQ ID NO 22
<211> LENGTH: 21
<212> TYPE: PRT
<213> ORGANISM: Rat

<400> SEQUENCE: 22

Thr Pro Asp Ile Asn Pro Ala Trp Tyr Thr Gly Arg Gly Ile Arg Pro
 1               5                  10                  15

Val Gly Arg Phe Gly
            20

<210> SEQ ID NO 23
<211> LENGTH: 22
<212> TYPE: PRT
<213> ORGANISM: Rat

<400> SEQUENCE: 23

Thr Pro Asp Ile Asn Pro Ala Trp Tyr Thr Gly Arg Gly Ile Arg Pro
 1               5                  10                  15

Val Gly Arg Phe Gly Arg
            20

<210> SEQ ID NO 24
<211> LENGTH: 93
<212> TYPE: DNA
<213> ORGANISM: Rat

<400> SEQUENCE: 24
agccgagccc accagcactc catggagaca agaaccctg atatcaatcc tgcctggtac      60
acgggccgcg ggatcaggcc tgtgggccgc ttc                                  93

<210> SEQ ID NO 25
<211> LENGTH: 96
<212> TYPE: DNA
<213> ORGANISM: Rat

<400> SEQUENCE: 25
agccgagccc accagcactc catggagaca agaaccctg atatcaatcc tgcctggtac      60
acgggccgcg ggatcaggcc tgtgggccgc ttcggc                               96

<210> SEQ ID NO 26
<211> LENGTH: 99
<212> TYPE: DNA
<213> ORGANISM: Rat

<400> SEQUENCE: 26
agccgagccc accagcactc catggagaca agaaccctg atatcaatcc tgcctggtac      60
acgggccgcg ggatcaggcc tgtgggccgc ttcggcagg                            99

<210> SEQ ID NO 27
<211> LENGTH: 60
<212> TYPE: DNA
<213> ORGANISM: Rat

<400> SEQUENCE: 27
```

```
accccctgata tcaatcctgc ctggtacacg ggccgcggga tcaggcctgt gggccgcttc        60
```

<210> SEQ ID NO 28
<211> LENGTH: 63
<212> TYPE: DNA
<213> ORGANISM: Rat

<400> SEQUENCE: 28

```
accccctgata tcaatcctgc ctggtacacg ggccgcggga tcaggcctgt gggccgcttc        60
ggc                                                                      63
```

<210> SEQ ID NO 29
<211> LENGTH: 66
<212> TYPE: DNA
<213> ORGANISM: Rat

<400> SEQUENCE: 29

```
accccctgata tcaatcctgc ctggtacacg ggccgcggga tcaggcctgt gggccgcttc        60
ggcagg                                                                   66
```

<210> SEQ ID NO 30
<211> LENGTH: 87
<212> TYPE: PRT
<213> ORGANISM: Human

<400> SEQUENCE: 30

```
Met Lys Val Leu Arg Ala Trp Leu Leu Cys Leu Leu Met Leu Gly Leu
 1               5                  10                  15

Ala Leu Arg Gly Ala Ala Ser Arg Thr His Arg His Ser Met Glu Ile
            20                  25                  30

Arg Thr Pro Asp Ile Asn Pro Ala Trp Tyr Ala Ser Arg Gly Ile Arg
        35                  40                  45

Pro Val Gly Arg Phe Gly Arg Arg Arg Ala Thr Leu Gly Asp Val Pro
    50                  55                  60

Lys Pro Gly Leu Arg Pro Arg Leu Thr Cys Phe Pro Leu Glu Gly Gly
65                  70                  75                  80

Ala Met Ser Ser Gln Asp Gly
                85
```

<210> SEQ ID NO 31
<211> LENGTH: 261
<212> TYPE: DNA
<213> ORGANISM: Human

<400> SEQUENCE: 31

```
atgaaggtgc tgagggcctg gctcctgtgc ctgctgatgc tgggcctggc cctgcgggga        60
gctgcaagtc gtacccatcg gcactccatg gagatccgca cccctgacat caatcctgcc       120
tggtacgcca gtcgcgggat caggcctgtg gccgcttcg gtcggaggag ggcaaccctg        180
ggggacgtcc ccaagcctgg cctgcgaccc cggctgacct gcttccccct ggaaggcggt       240
gctatgtcgt cccaggatgg c                                                 261
```

<210> SEQ ID NO 32
<211> LENGTH: 31
<212> TYPE: PRT
<213> ORGANISM: Human

<400> SEQUENCE: 32

```
Ser Arg Thr His Arg His Ser Met Glu Ile Arg Thr Pro Asp Ile Asn
```

```
                1               5                  10                15
        Pro Ala Trp Tyr Ala Ser Arg Gly Ile Arg Pro Val Gly Arg Phe
                        20                  25                  30
```

<210> SEQ ID NO 33
<211> LENGTH: 32
<212> TYPE: PRT
<213> ORGANISM: Human

<400> SEQUENCE: 33

```
        Ser Arg Thr His Arg His Ser Met Glu Ile Arg Thr Pro Asp Ile Asn
        1               5                   10                  15
        Pro Ala Trp Tyr Ala Ser Arg Gly Ile Arg Pro Val Gly Arg Phe Gly
                        20                  25                  30
```

<210> SEQ ID NO 34
<211> LENGTH: 33
<212> TYPE: PRT
<213> ORGANISM: Human

<400> SEQUENCE: 34

```
        Ser Arg Thr His Arg His Ser Met Glu Ile Arg Thr Pro Asp Ile Asn
        1               5                   10                  15
        Pro Ala Trp Tyr Ala Ser Arg Gly Ile Arg Pro Val Gly Arg Phe Gly
                        20                  25                  30
        Arg
```

<210> SEQ ID NO 35
<211> LENGTH: 20
<212> TYPE: PRT
<213> ORGANISM: Human

<400> SEQUENCE: 35

```
        Thr Pro Asp Ile Asn Pro Ala Trp Tyr Ala Ser Arg Gly Ile Arg Pro
        1               5                   10                  15
        Val Gly Arg Phe
                        20
```

<210> SEQ ID NO 36
<211> LENGTH: 21
<212> TYPE: PRT
<213> ORGANISM: Human

<400> SEQUENCE: 36

```
        Thr Pro Asp Ile Asn Pro Ala Trp Tyr Ala Ser Arg Gly Ile Arg Pro
        1               5                   10                  15
        Val Gly Arg Phe Gly
                        20
```

<210> SEQ ID NO 37
<211> LENGTH: 22
<212> TYPE: PRT
<213> ORGANISM: Human

<400> SEQUENCE: 37

```
        Thr Pro Asp Ile Asn Pro Ala Trp Tyr Ala Ser Arg Gly Ile Arg Pro
        1               5                   10                  15
        Val Gly Arg Phe Gly Arg
                        20
```

<210> SEQ ID NO 38

```
<211> LENGTH: 93
<212> TYPE: DNA
<213> ORGANISM: Human

<400> SEQUENCE: 38
agtcgtaccc atcggcactc catggagatc cgcaccctg acatcaatcc tgcctggtac      60
gccagtcgcg ggatcaggcc tgtgggccgc ttc                                  93

<210> SEQ ID NO 39
<211> LENGTH: 96
<212> TYPE: DNA
<213> ORGANISM: Human

<400> SEQUENCE: 39
agtcgtaccc atcggcactc catggagatc cgcaccctg acatcaatcc tgcctggtac      60
gccagtcgcg ggatcaggcc tgtgggccgc ttcggt                               96

<210> SEQ ID NO 40
<211> LENGTH: 99
<212> TYPE: DNA
<213> ORGANISM: Human

<400> SEQUENCE: 40
agtcgtaccc atcggcactc catggagatc cgcaccctg acatcaatcc tgcctggtac      60
gccagtcgcg ggatcaggcc tgtgggccgc ttcggtcgg                            99

<210> SEQ ID NO 41
<211> LENGTH: 60
<212> TYPE: DNA
<213> ORGANISM: Human

<400> SEQUENCE: 41
acccctgaca tcaatcctgc ctggtacgcc agtcgcggga tcaggcctgt gggccgcttc     60

<210> SEQ ID NO 42
<211> LENGTH: 63
<212> TYPE: DNA
<213> ORGANISM: Human

<400> SEQUENCE: 42
acccctgaca tcaatcctgc ctggtacgcc agtcgcggga tcaggcctgt gggccgcttc     60
ggt                                                                   63

<210> SEQ ID NO 43
<211> LENGTH: 66
<212> TYPE: DNA
<213> ORGANISM: Human

<400> SEQUENCE: 43
acccctgaca tcaatcctgc ctggtacgcc agtcgcggga tcaggcctgt gggccgcttc     60
ggtcgg                                                                66

<210> SEQ ID NO 44
<211> LENGTH: 31
<212> TYPE: PRT
<213> ORGANISM: Unknown
<220> FEATURE:
<221> NAME/KEY:
<223> OTHER INFORMATION: Xaa on the 3rd position means Thr or Ala, Xaa
      on the 5th position means Arg or Gln, Xaa on the 10th position
      means Ile or Thr, Xaa on the 21st position means Thr or Ala, Xaa
      on the 22nd position means Gly or Ser.
```

```
<400> SEQUENCE: 44

Ser Arg Xaa His Xaa His Ser Met Glu Xaa Arg Thr Pro Asp Ile Asn
1               5                   10                  15

Pro Ala Trp Tyr Xaa Xaa Arg Gly Ile Arg Pro Val Gly Arg Phe
                20              25                  30

<210> SEQ ID NO 45
<211> LENGTH: 20
<212> TYPE: PRT
<213> ORGANISM: Unknown
<220> FEATURE:
<221> NAME/KEY:
<223> OTHER INFORMATION: Xaa on the 10th position means Thr or Ala, Xaa
      on the 11th position means Gly or Ser.

<400> SEQUENCE: 45

Thr Pro Asp Ile Asn Pro Ala Trp Tyr Xaa Xaa Arg Gly Ile Arg Pro
1               5                   10                  15

Val Gly Arg Phe
            20
```